(12) United States Patent
Koh et al.

(10) Patent No.: US 11,666,325 B2
(45) Date of Patent: Jun. 6, 2023

(54) AUTOMATED SEWING AND THREAD MANAGEMENT

(71) Applicant: Edwards Lifesciences Corporation, Irvine, CA (US)

(72) Inventors: Wei Nee Koh, Singapore (SG); Ping-Yang Shih, Santa Ana, CA (US); Marius Tomas Petrulis, Long Beach, CA (US); Sam Nicolas Sarian, Glendale, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 19 days.

(21) Appl. No.: 16/938,814

(22) Filed: Jul. 24, 2020

(65) Prior Publication Data

US 2021/0378663 A1    Dec. 9, 2021

Related U.S. Application Data

(63) Continuation of application No. PCT/US2020/036752, filed on Jun. 9, 2020.

(51) Int. Cl.
*A61B 17/04* (2006.01)
*A61F 2/24* (2006.01)

(52) U.S. Cl.
CPC ...... *A61B 17/0491* (2013.01); *A61B 17/0482* (2013.01); *A61F 2/2409* (2013.01); *A61F 2220/0075* (2013.01)

(58) Field of Classification Search
CPC ............. A61B 17/0491; A61B 17/0482; A61F 2/2409; A61F 2220/0075
See application file for complete search history.

(56) References Cited

U.S. PATENT DOCUMENTS

| | | | |
|---|---|---|---|
| 3,347,190 A | 10/1967 | Roth | |
| 3,709,175 A | 1/1973 | Edwards et al. | |
| 3,710,744 A | 1/1973 | Goodenough et al. | |
| 4,035,849 A | 7/1977 | Angell et al. | |
| 4,205,616 A | 6/1980 | Sugahara | |

(Continued)

FOREIGN PATENT DOCUMENTS

| | | | |
|---|---|---|---|
| WO | 9530387 A1 | 11/1995 | |
| WO | 9640012 A1 | 12/1996 | |

(Continued)

*Primary Examiner* — Sarah A Simpson
*Assistant Examiner* — Raihan R Khandker
(74) *Attorney, Agent, or Firm* — Edwards Lifesciences; David S. Barnhill

(57) ABSTRACT

The present disclosure relates to automated systems, devices, and methods of sewing a target device such as a prosthetic implant device. The systems and methods include forming a stitch on the target device, adjusting a thread coupled to a needle used to form the stitch so that the thread is clear of (e.g., does not interfere with) a path of the needle, and applying a targeted tension to the thread to tension the stitch on the target device. The suturing process can also include providing different targeted tensions during formation of the stitch. The suturing process can also include providing different targeted tensions at different stages of the formation of the stitch to aid in forming the stitch, to clear the needle path of the thread, and/or to hold the stitch in place in preparation for the next stitch.

15 Claims, 14 Drawing Sheets

(56) References Cited

U.S. PATENT DOCUMENTS

| | | |
|---|---|---|
| 4,388,735 A | 6/1983 | Ionescu et al. |
| 4,414,908 A * | 11/1983 | Eguchi ............... A61B 17/0491 606/147 |
| 4,437,465 A * | 3/1984 | Nomoto ................ D05B 81/00 112/276 |
| 4,626,255 A | 12/1986 | Reichart et al. |
| 4,680,031 A | 7/1987 | Alonso |
| 5,095,833 A | 3/1992 | Darrieux |
| 5,488,789 A | 2/1996 | Religa et al. |
| 5,895,420 A | 4/1999 | Mirsch, II et al. |
| 5,928,281 A | 7/1999 | Huynh et al. |
| 6,189,747 B1 | 2/2001 | Collingham et al. |
| 6,295,940 B1 | 10/2001 | Shonteff |
| 6,338,740 B1 | 1/2002 | Carpentier |
| 6,453,062 B1 | 9/2002 | MacNutt et al. |
| 6,558,418 B2 | 5/2003 | Carpentier et al. |
| 6,736,845 B2 | 5/2004 | Marquez et al. |
| 6,755,141 B2 | 6/2004 | Musco et al. |
| 7,073,456 B2 | 7/2006 | Phillips et al. |
| 7,185,597 B1 | 3/2007 | Phillips et al. |
| 7,481,838 B2 | 1/2009 | Carpentier et al. |
| 7,739,971 B2 | 6/2010 | Chambers et al. |
| 8,276,533 B2 | 10/2012 | Chambers et al. |
| 9,301,835 B2 | 4/2016 | Campbell et al. |
| 9,339,378 B2 | 5/2016 | Quadri et al. |
| 10,119,882 B2 | 11/2018 | Van Nest et al. |
| 2004/0176839 A1 | 9/2004 | Huynh et al. |
| 2005/0013841 A1 | 1/2005 | Phillips et al. |
| 2006/0276889 A1 | 12/2006 | Chambers et al. |
| 2008/0035038 A1 | 2/2008 | Ekholm et al. |
| 2010/0257735 A1 | 10/2010 | Chambers et al. |
| 2014/0033959 A1 | 2/2014 | Evans et al. |
| 2015/0073443 A1 * | 3/2015 | Chen ................ A61B 17/0491 606/148 |
| 2017/0325976 A1 | 11/2017 | Nguyen et al. |
| 2018/0250129 A1 | 9/2018 | Koral et al. |

FOREIGN PATENT DOCUMENTS

| | | |
|---|---|---|
| WO | 0182781 A2 | 11/2001 |
| WO | 2008016760 A2 | 2/2008 |
| WO | 2015070249 A1 | 5/2015 |
| WO | 2018156767 A1 | 8/2018 |
| WO | 2019140293 A1 | 7/2019 |
| WO | 2020041558 A1 | 2/2020 |

\* cited by examiner

AUTOMATED SEWING AND THREAD MANAGEMENT

CROSS-REFERENCE TO RELATED APPLICATIONS

This application claims priority to, and is a continuation of, International Patent Application No. PCT/US2020/036752, filed Jun. 9, 2020, which is incorporated herein in its entirety for all purposes.

BACKGROUND

Medical devices, prosthetic implants, prosthetic heart valves, etc. can require sewing, treatment, inspection, etc. of certain portions and/or components thereof. Accuracy and/or efficiency in execution of suturing or other operations for such devices and other devices can be important. Furthermore, certain suturing operations or other operations can be time consuming and difficult.

SUMMARY

This summary is meant to provide some examples and is not intended to be limiting of the scope of the disclosed subject matter in any way. For example, any feature included in an example of this summary is not required by the claims, unless the claims explicitly recite the features. Also, the features, steps, concepts, etc. described in examples in this summary and elsewhere in this disclosure can be combined in a variety of ways. The description herein relates to devices, apparatuses, systems, assemblies, methods, combinations, etc. that can be utilized for manufacturing and processing heart valves and/or associated or related components, devices, apparatuses, etc.

In some implementations, the present disclosure relates to an automated method of manufacturing (e.g., sewing or suturing) a target device or component such as a prosthetic implant device (e.g., a prosthetic human implant device, prosthetic heart valve, prosthetic human heart valve, etc.). The method includes forming a stitch on the target device, adjusting a thread coupled to a needle used to form the stitch so that the thread is clear of a path of the needle (e.g., the thread does not interfere with the needle path), and applying a targeted tension to the thread to tension the stitch on the target device. The method can be automated.

In some implementations, the method also includes providing a plurality of targeted tensions during formation of the stitch. For example, the method can include providing a targeted tension that changes as a function of time and/or stage of the formation of the stitch. The plurality of targeted tensions can be applied at different stages of the formation of the stitch to aid in clearing the needle path of the thread and/or to hold the stitch in place in preparation for the next stitch. At one or more stages in the formation of the stich, tension may be substantially released from the thread.

In some implementations, a method of sewing an implant device includes passing a needle with a thread from a first needle gripper to a second needle gripper to form a first portion of a stitch on the implant device, passing the needle with the thread from the second needle gripper back to the first needle gripper to form a second portion of the stitch on the implant device, moving the thread out of a path of the needle or needle path, and applying tension to the thread. The first needle gripper and the second needle gripper and movements thereof can be automated. In some embodiments, the needle path can be a fixed linear path (e.g., a path along a line or along an axis, etc.), and the method can include moving the needle back and forth along the fixed linear path. As described herein, the tension on the thread can vary over time and/or stage of the formation of the stitch and the tension may be removed at one or more points in time during formation of the stitch.

In some embodiments, applying tension to the thread includes applying a plurality of different tensions at different times to form the suture and/or to hold the suture down. Clearing the needle path of the thread can include moving a portion of the thread between the implant device and the first needle gripper in a direction orthogonal to the needle path.

In some implementations, a suturing system includes one or more automated fixtures or systems. For example, the suturing system includes a first automated fixture that includes a plurality of actuator devices and a holder or target device holder. The first automated fixture is configured to move or rotate a target device (e.g., a heart valve, component of a heart valve, etc.), for example, when the target device is mounted to the holder or target device holder. The suturing system includes a second automated fixture includes one or more needle grippers and a plurality of actuator devices. The second automated fixture is configured to pass a needle back and forth through a surface of the target device to form stitches or sutures on the target device. The suturing system includes an automated thread management system for moving the thread and providing tension on the thread. The automated thread management system includes a tensioning device that can provide a targeted tension on a suture when forming sutures on the target device. The automated thread management system also includes a thread movement device that moves thread out of a path of the needle or needle path defined by the second automated fixture. The needle path can be a fixed linear path, e.g., a path along an axis or along a line.

In some implementations, the automated thread management system provides an increasing tension during a first phase of a suturing process and a targeted tension during a second phase of the suturing process. In some implementations, the automated thread management system transitions to the targeted tension responsive to exceeding a tension threshold during the first phase of the suturing process. In certain implementations, the automated thread management system removes tension during a third phase of the suturing process.

In some embodiments, the needle is a double-sided needle with an eye near a middle of the needle. In such embodiments, the second automated fixture can be configured to maintain the orientation of the needle when passing the needle back and forth through a surface of the target device (e.g., the needle is not rotated 180 degrees while forming a stitch).

In some embodiments, the second automated fixture is configured to move the needle along a fixed path. In such embodiments, the first automated fixture is configured to adjust a position and/or orientation of the target device during formation of a suture so that the suture is made at a targeted location on the target device. In further embodiments, the fixed path is a linear path or a path along an axis or along a straight line. In certain embodiments, the fixed path can be curved or can be a combination of straight and curved portions.

In some embodiments, the first automated fixture and the second automated fixture of the system are arranged relative to each other and configured such that the first automated fixture can move the target device in three dimensions to position and orient the target device in the path of the needle.

The suturing system and component or fixtures thereof can be configured to implement a predetermined suturing pattern on the target device. In some embodiments, the first automated fixture comprises a first controller configured to direct the first automated fixture how to position the target device. In some embodiments, the second automated fixture comprises a second controller configured to direct the second automated fixture when to move the needle to implement the suturing pattern.

In some embodiments, the automated thread management system includes a third controller configured to direct the thread movement device to move the thread out of the needle path. The third controller can also be configured to direct the tensioning device to apply tension to the thread. The third controller can also be configured to change the tension applied to the thread. In certain embodiments, functionality of two or more of the first controller, the second controller, and the third controller are combined in a controller for the suturing system. The needle path can be a fixed linear path, e.g., a path along an axis or along a straight line, a fixed curved path, e.g., a path along a curve, or a fixed path that is a combination of a linear and curved paths, e.g., a path with one or more straight portions and one or more curved portions. The needle path can be the path repeatedly traverses when forming stitches on the target device. A suturing pattern can be achieved on the target device using the fixed needle path by adjusting a position and/or orientation of the target device during and/or between stitches.

In some implementations, a thread management system is provided that comprises a thread movement device configured to move a thread to clear the needle path for an automated suturing system. Movement of the thread can be in a direction orthogonal to a needle path. The thread management system can also include a tensioning device configured to apply a targeted tension to the thread to form a stitch in a target device.

In some implementations, the tensioning device is configured to provide an increasing tension until reaching a tension threshold and to provide a steady state tension after the increasing tension exceeds the tension threshold. In certain implementations, the tensioning device is configured to provide different tensioning phases while forming the stitch, the different tensioning phases including an increasing tension phase, a decreasing tension phase, a steady state tensioning phase, and a tension release phase. In further implementations, the increasing tension phase can proceed to the decreasing tension phase once the tension increases over a threshold. The decreasing tension phase can proceed to the steady state tension phase, which is less than the threshold tension, once the decreasing tension reaches the steady state tension. The steady state tension phase can proceed to the tension release phase at a particular stage during formation of the stitch. The tensioning phases can be repeated in harmony with movement of the needle to form stitches on the target device.

The thread management system can be used in the automated suturing systems described above or elsewhere herein. For example, the thread management system can be used with, and can be a part of, an automated suturing system that includes a first automated fixture with a holder, the first automated fixture being configured to adjust an orientation of a target device when held by the holder, and a second automated fixture with a first needle gripper and a second needle gripper that are configured to pass a needle back and forth through a surface of the target device to form sutures.

In some implementations, a method of suturing or sewing a target device includes operating an automated suturing system to suture or sew a target device, wherein the automated suturing system is programmed to perform programmed steps. In some embodiments, the programmed steps include passing, using a first needle gripper and a second needle gripper, a needle through a surface of the target device, the first needle gripper moving toward the target device along a needle path (e.g., a fixed path, a fixed linear path, a path along an axis or straight line, a curved path, etc.) and adjusting a position of the target device. In some embodiments, the programmed steps include passing, using the first needle gripper and the second needle gripper, the needle back through the surface of the target device. The first needle gripper can be programmed to move with the needle away from the target device along the needle path. In some embodiments, the programmed steps also include moving a thread coupled to the needle so that it is clear of the needle path and applying a targeted tension to the thread.

Applying the targeted tension can include applying an increasing tension until a tension threshold is exceeded, and then applying a steady state tension after the tension threshold has been exceeded. In some embodiments, the tension threshold is greater than or equal to about 0.4 N. In some embodiments, the steady state tension is less than or equal to about 0.3 N. In some embodiments, the programmed steps further include releasing tension on the thread after applying the steady state tension to the thread.

Moving the thread to clear the needle path can include moving the thread orthogonal to the needle path. Adjusting the position of the target device can include rotating the target device. Also, adjusting the position of the target device can include moving the target device orthogonal to the needle path.

Operating the automated suturing system to suture a target device comprises causing the automated suturing system to perform the programmed steps (e.g., any and/or all of the programmed steps).

In some implementations, a method of suturing a target device comprises operating an automated suturing system, wherein the automated suturing system is programmed to perform multiple suturing steps. In some embodiments, the automated suturing system is programmed to pass, using a first needle gripper and a second needle gripper, a needle through a surface of the target device, the first needle gripper moving toward the target device along a needle path; to adjust a position of the target device; and to pass, using the first needle gripper and the second needle gripper, the needle back through the surface of the target device. The first needle gripper can be programmed to move away from the target device along the needle path.

In some embodiments, the automated suturing system is programmed to move a thread coupled to the needle so that it is clear of the needle path. In some embodiments, the automated suturing system is programmed to apply a targeted tension to the thread.

In some implementations, an automated suturing system is programmed to pass, using a first needle gripper and a second needle gripper, a needle through a surface of the target device, the first needle gripper moving toward the target device along a needle path (e.g., a fixed path, a fixed linear path, a path along an axis or straight line, a curved path, etc.). The automated suturing system can also be programmed to adjust a position of the target device, and pass, using the first needle gripper and the second needle gripper, the needle back through the surface of the target device. The first needle gripper can be programmed to move away from the target device along the needle path.

In some embodiments, the automated suturing system is also programmed to move a thread coupled to the needle so that it is clear of the needle path and to apply a targeted tension to the thread. The automated suturing system can be programmed to apply the targeted tension such that an increasing tension is applied for a period of time and then a steady state tension is applied after the increasing tension exceeds a tension threshold. In certain implementations, the tension threshold can be greater than or equal to about 0.4 N. In various implementations, the steady state tension can be less than or equal to about 0.3 N. The automated suturing system can further be programmed to release tension on the thread after applying the targeted tension to the thread.

The automated suturing system can be programmed to move the thread to clear the needle path. For example, the thread can be moved orthogonal to the needle path to clear it. The automated suturing system can be programmed to adjust a position of the target device. For example, the target device can be rotated and/or moved orthogonal to the needle path.

Other steps, features, components, etc. not specifically mentioned in these examples, but described elsewhere herein or otherwise known can also be included and/or used with the examples described here.

BRIEF DESCRIPTION OF THE DRAWINGS

Various embodiments are depicted in the accompanying drawings for illustrative purposes and should in no way be interpreted as limiting the scope of any of the inventions disclosed herein. In addition, various features of different disclosed embodiments can be combined to form additional embodiments, which are part of this disclosure. Throughout the drawings, reference numbers may be reused to indicate correspondence between reference elements.

FIGS. 10A, 10B, 100, 10D, and 10E illustrate portions of an example suturing process performed by certain components of an example automated suturing system, such as that of FIG. 8.

DETAILED DESCRIPTION

Figure 1:
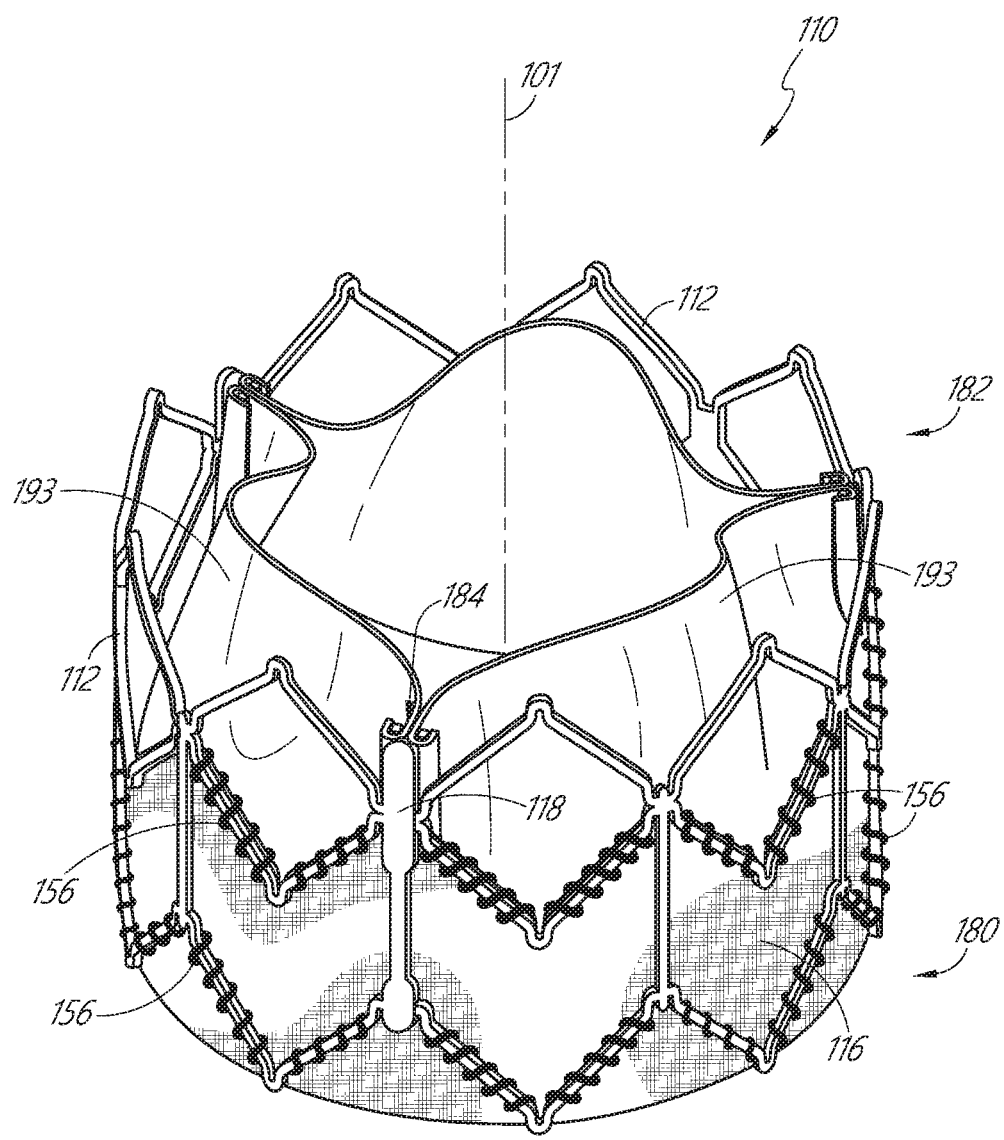
FIG. 1 illustrates an example of an implantable prosthetic valve device.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Further, one or more steps disclosed with respect to one method may be incorporated into other methods disclosed herein. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein. Features described with respect to one exemplary embodiment may be incorporated into other embodiments disclosed herein even if not specifically described with respect to the embodiment.

Overview

Prosthetic heart valve implants, as well as many other types of prosthetic implant devices and other types of devices, can comprise various sutured components and/or portions. For example, a sealing portion, skirt, etc. can be sutured to a frame of a prosthetic heart valve to help prevent blood from leaking around the outer edges or circumference of the prosthetic heart valve. Execution of sutures or stitches by a human operator may be relatively difficult and/or cumbersome in certain conditions. For example, where small stitches are to be made with high precision, the complexity and/or associated operator burden may result in discomfort and/or undesirably low quality of products. Furthermore, certain heart valve implant devices may require hundreds of sutures, which can involve substantially labor-intensive and error-susceptible suturing procedures. Therefore, adding automation to suturing of implants can be desirable to improve quality, speed of manufacture, and/or help prevent issues associated with human operators.

Certain embodiments disclosed herein provide automated heart valve suturing systems, devices, and/or methods for performing suturing procedures involving the physical manipulation and/or positioning of one or more automated mechanical articulating fixtures, components, and/or subassemblies, using automated needle grippers to manipulate a needle to form sutures or stitches on the target heart valve, and using automated mechanical systems to apply tension to the sutures and to move thread out of the path of the needle. Such articulating fixture(s) or component(s) may be configured to hold or secure a prosthetic human heart valve implant device, or other suturing subject or implant device having one or more components or portions that may advantageously be sutured together. Such automated needle grippers can be configured to pass a needle back and forth through a surface or material of the target heart valve to form sutures. Such automated mechanical systems can be configured to move a thread out of a path of the needle and/or to tension the thread to form sutures. The various embodiments relating to heart valve suturing presented herein can be applicable to heart valves having any type of suturing and/or structural configuration or pattern. Examples of heart valve structures and heart valve suturing techniques that may be applicable to certain embodiments presented herein are disclosed in WIPO Publication No. WO 2015/070249, the entire contents of which is hereby expressly incorporated by reference herein.

FIG. 1 illustrates an example implantable prosthetic human valve device 110 according to one or more embodiments, but a variety of other variations and designs of valve devices are also possible. The features of valve 110 described herein can apply to other valves, including other valves or target devices described elsewhere herein. The valve 110 can be, for example, a transcatheter heart valve (THV), balloon-expandable heart valve, and/or mechanically-expandable heart valve. The valve 110 in the illustrated embodiment can generally comprise a frame or stent 112, a leaflet structure 193 supported by the frame 112, and a sealing member or skirt 116 secured (e.g., sutured or stitched) to the outer surface of the leaflet structure 193. In certain embodiments, the valve 110 is configured to be implanted in the annulus of a native heart valve of a human, such as an aortic valve. However, the valve 110 can additionally or alternatively be adapted to be implanted in other native valves of the heart, or in various other vasculature, ducts, or orifices of the body, or in grafts, docking stents, docking stations, rings, etc. implanted in the body. The lower end 180 of the valve 110, according to the illustrated orientation, represents an inflow end, while the upper end 182 of the valve 110, according to the illustrated orientation, represents an outflow end.

The valve 110 and the frame 112 can be configured to be radially collapsible to a collapsed or crimped state or configuration for introduction into the body using a delivery catheter, and further can be configured to be radially expandable to an expanded state or configuration for implanting the valve at a desired location in the body (e.g., the native aortic valve, etc.). In certain embodiments, the frame 112 comprises a plastic, polymer, shape memory material, or metal expandable material that permits crimping of the valve 110 to a smaller profile for delivery and expansion of the valve. In certain implementations, an expansion device, such as the balloon of a balloon catheter or a tool for mechanical expansion, can be used to expand or help expand the valve. In certain embodiments, the valve 110 is a self-expanding valve, wherein the frame is made of a self-expanding material such as a shape memory material or metal (e.g., Nitinol). Self-expanding valves can be able to be crimped to a smaller profile and held in the crimped state with a restraining device, such as a sheath covering the valve. When the valve is positioned at or near the target site, the restraining device can be removed or retracted to allow the valve to self-expand to its expanded, functional size or to a deployed configuration.

The sealing portion or skirt 116 can comprise a single piece or multiple pieces or material (e.g., cloth, polymer, etc.) with opposite ends that are secured to each other to form the annular shape illustrated in FIG. 1 or extend around a circumference of the valve. In certain embodiments, the upper edge of the sealing portion or skirt 116 has an undulating shape that generally follows the shape of struts of the frame 112. In this manner, the upper edge portions of the sealing portion or skirt 116 can be tightly secured to respective struts with sutures 156. The sealing portion or skirt 116 can be placed on the outside of the frame 112 or on the inside of the frame 112 (as illustrated) and an upper edge portion of the sealing portion or skirt 116 can be wrapped around the upper surfaces of the frame struts and secured in place with sutures. The sutures 156 provide a durable attachment of the sealing portion or skirt 116 to the frame 112.

The leaflet structure 193 can comprise three leaflets (as illustrated in FIG. 1) in certain embodiments, which can be arranged to collapse in a tricuspid arrangement. Although a three-leaflet embodiment is illustrated, it should be understood that valve implants sutured according to embodiments disclosed herein can have any number of leaflets, such as, for example, two or four. The leaflets 193 can be formed from separate flaps of material or tissue or all three leaflets can be derived from a single material. The lower edge of leaflet structure 193 can have a variety of shapes. In certain embodiments, the lower edge of the leaflet structure 193 can have an undulating, curved, and/or scalloped shape that can be sutured to the frame 112. The leaflets 193 can be secured to one another at their adjacent sides to form commissures 184 of the leaflet structure, where the edges of the leaflets come together. The leaflet structure 193 can be secured to the frame 112 using any suitable techniques and/or mechanisms. For example, the commissures 184 of the leaflet structure can be aligned with the support posts 118 and secured thereto, e.g., using sutures, adhesive, clamping portions, crimping, and/or other attachment means. In certain implementations, the point of attachment of the leaflets 193 to the posts 118 can be reinforced, e.g., with bars comprising a more rigid material or stainless steel.

Figure 2:
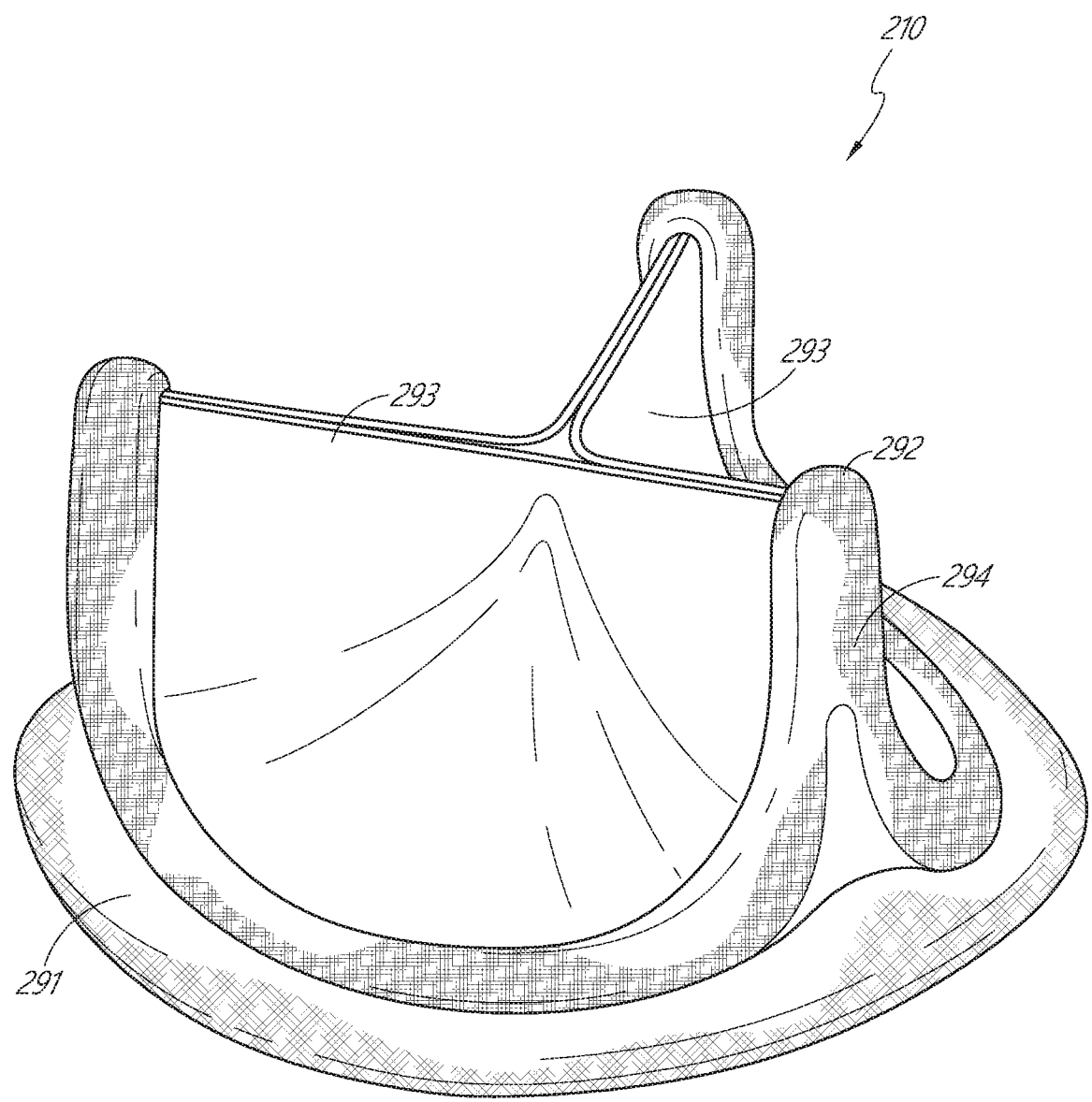
FIG. 2 illustrates a perspective view of an example of another prosthetic heart valve.

FIG. 2 illustrates a perspective view of an example prosthetic human heart valve 210 in accordance with one or more embodiments. The heart valve 210 can include a peripheral sealing ring structure 291 configured to provide support for nesting the heart valve 210 in a heart valve cavity and/or resting upon, or attached to, an annulus or other structure of the heart. The valve 210 can further include a frame member 292, such as a metal frame, which can provide support for a plurality of flexible leaflets 293 and can define three upstanding commissure posts 294, wherein the leaflets 293 can be supported between the commissure posts 294. In certain implementations, as illustrated in FIG. 2, the sealing ring 291 can attach around the periphery of the frame member 292 at the inflow end of the valve 210, with the commissure posts 294 projecting in the outflow direction.

The leaflets 293 can be formed from separate flaps of material or tissue or all three leaflets can be derived from a single material. The leaflets 293 can be secured and supported both by the commissure posts 294, as well as along arcuate cusps of the frame member 292 between the commissure posts 294.

Figure 3A:
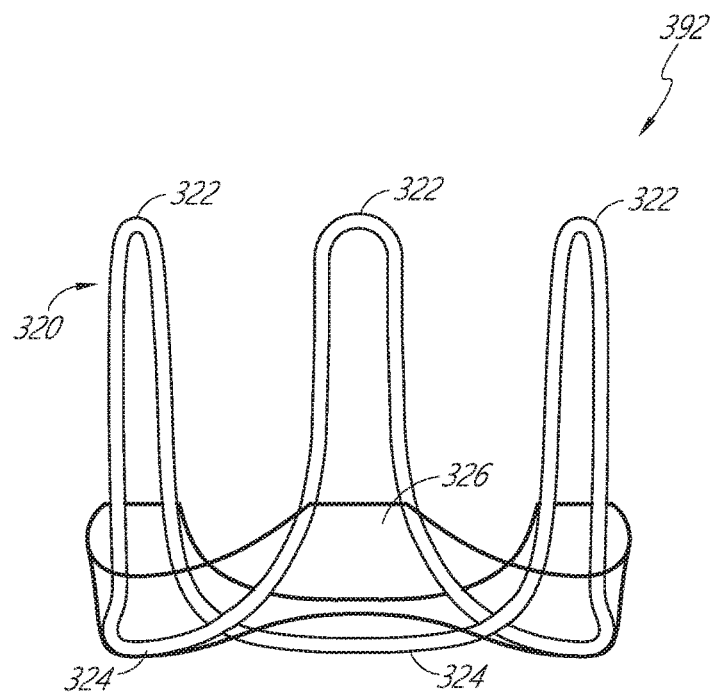
FIG. 3A illustrates a frame for a support stent for an example surgical valve.

FIG. 3A illustrates a frame 392 for a support stent for a surgical heart valve such as the valve 210 of FIG. 2. The frame 392 can include multiple cusps curved toward an axial inflow end alternating with multiple commissures 322 projecting toward an axial outflow end, the support stent 392 defining an undulating outflow edge. The support stent 392 can comprise a wireform 320 having three upstanding commissures 322 alternating with three cusps 324 which generally circumscribe a circumference. A stiffening band 326 can be disposed within or without the wireform 320. The inflow edge of the band 326 can conform or at least partially conform to the cusps 324 of the wireform 320 and can be curved in the outflow direction in between in the region of the wireform commissures 322, e.g., as illustrated in FIG. 3A. In some embodiments, the support stent 392 provides the supporting structure of a one-way prosthetic heart valve, an example of which is the valve 210 described herein with reference to FIG. 2.

Figure 3B:
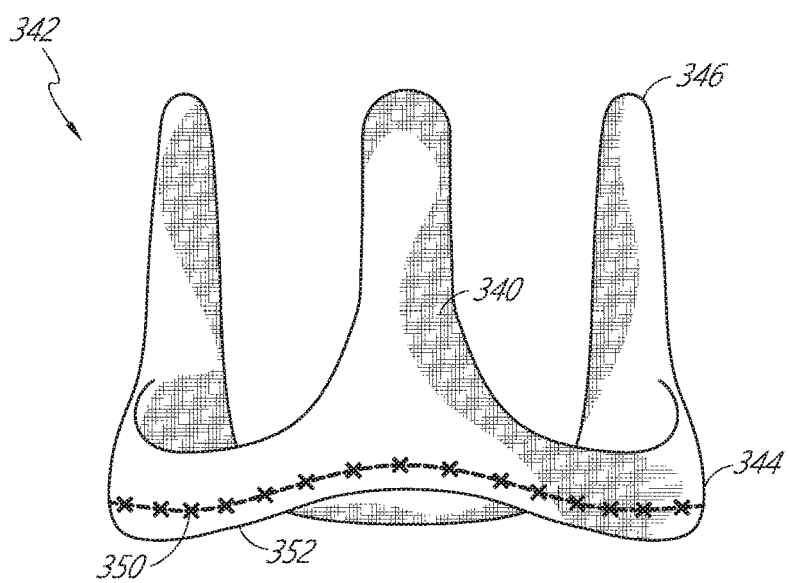
FIG. 3B illustrates the frame of FIG. 3A covered with fabric.

FIG. 3B illustrates the frame of FIG. 3A covered with fabric 340, wherein the fabric 340 can be sutured in one or more portions to secure the fabric 340 as a covering for the frame 392. The fabric-covered support stent 342 can be generally tubular and can include multiple cusps 344 curved toward an axial inflow end alternating with multiple commissures 346 projecting toward an axial outflow end. The support stent 342 can comprise an undulating outflow edge about which the fabric 340 is secured held. In certain embodiments, a seam 350 is sutured adjacent an inflow edge 352 that secures the fabric 340 about the support stent 342. The seam 350 is illustrated slightly axially above the inflow edge 352 for clarity, although it can be located directly at the inflow edge or even inside the support stent 342. In certain implementations, one or more seams can be located in other positions along the fabric 340. The sutures of the support stent 342 can be executed or added in multiple ways, such as using the devices and systems disclosed herein. Furthermore, although certain sutures are illustrated in FIG. 3B, the support stent 342 and/or valve implant 210 of FIG. 2 can comprise any type or number of sutures or stitches. For example, the support stent 342 and/or one or more other components of the associated implant device, can also have leaflets and/or other materials sutured thereto.

Figure 4:
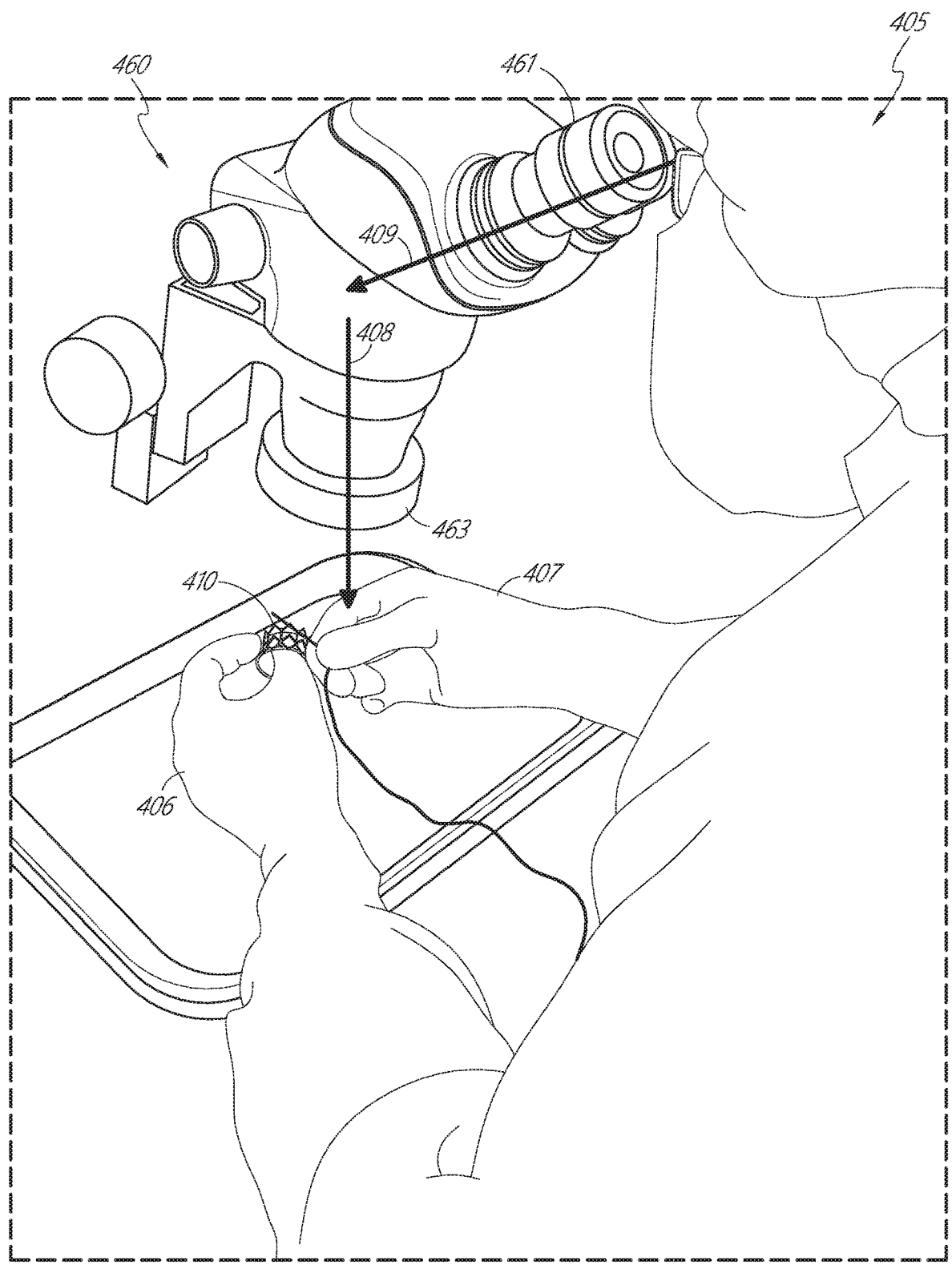
FIG. 4 illustrates an example of an operator performing operations on an implant device.

Suturing of prosthetic heart valve devices and/or other implant devices, such as those described above, can be performed in various ways. For example, certain handheld processes for suturing prosthetic human implant devices may be implemented in which an operator utilizes both hands for holding, securing, and/or suturing the implant device. FIG. 4 illustrates an operator 405 performing operations on a prosthetic human implant device 410. For example, the operator 405 can suture an outer wireframe of the device 410 to an inner skirt or cloth, as described above, where the implant device 410 is a transcatheter heart valve device. Alternatively, the implant device 410 can be a surgical valve device, or other type of implant device. The implant device 410 can be the same as or similar to one of the valves illustrated herein or can be a different type of valve or implant device.

As illustrated in the diagram of FIG. 4, in some processes, an operator 405 may need to use both hands to execute relevant suturing operations. For example, a first hand 406 may be used to hold and/or secure the implant device 410, and a second hand 407 may be used to manually operate a suturing needle or the like.

For the operator 405 to effectively execute the relevant suturing operations on the implant device 410, it may be necessary or desirable for the view of the implant device 410 to be magnified or otherwise enhanced in some manner. For example, as illustrated, the operator may further utilize a magnification system 460, such as a microscope, which may comprise an eyepiece component 461 as well as one or more lenses and/or refractive elements 463. In certain embodiments, the magnification system 460 is designed such that the operator 405 may have a line of sight 409 at a first angle, wherein the magnification system 460 is configured to at least partially reflect light therein at a downward angle 408 to focus on a target focal plane below.

Figure 5:
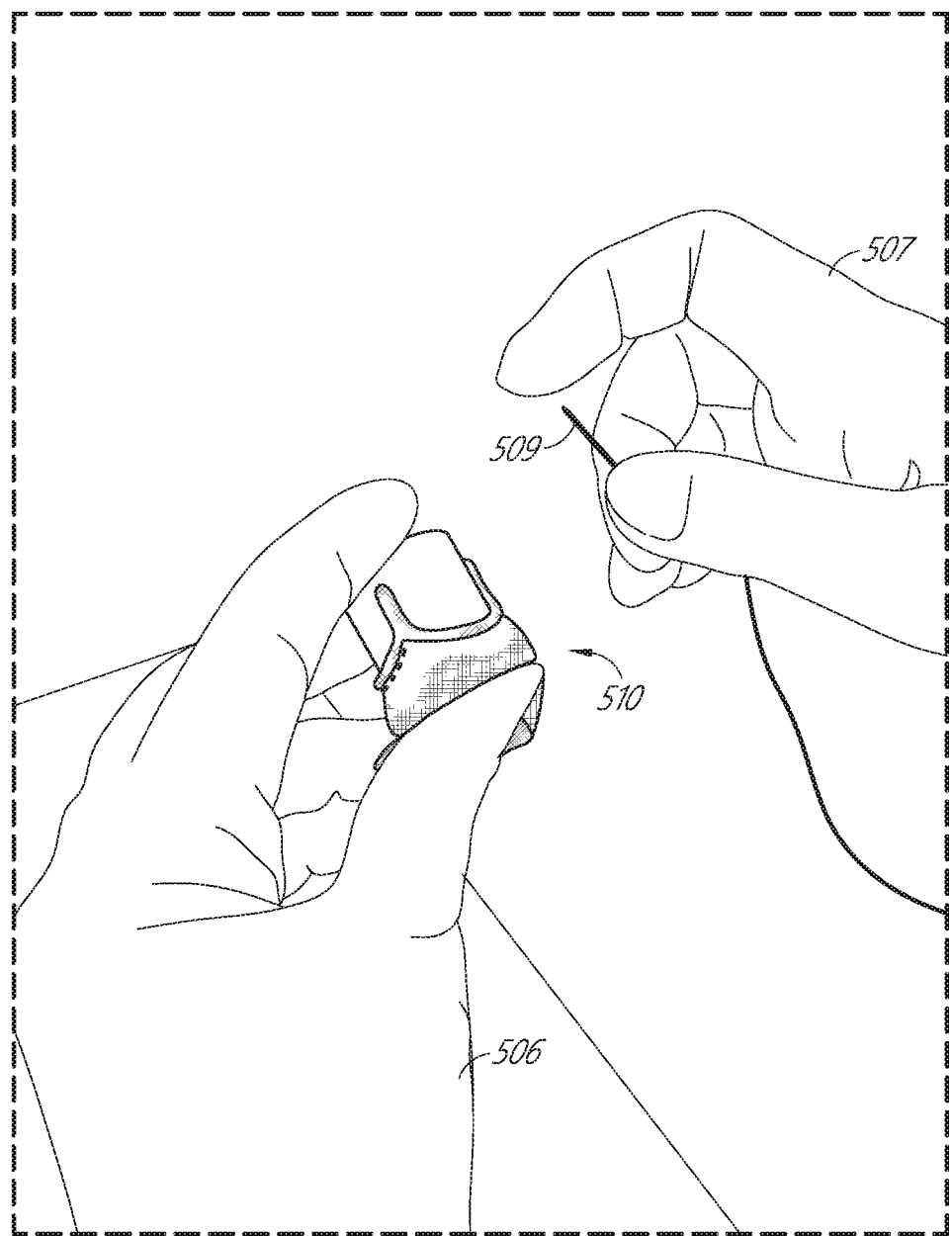
FIG. 5 illustrates a close-up view of a heart valve implant device being sutured using manual holding and suturing.

FIG. 5 illustrates a close-up view of a prosthetic human implant device 510 being sutured using manual holding and suturing, as described above. As illustrated, for handheld suturing solutions, a first hand 506 may be required to hold the target implant device 510, while a second hand 507 may be required to manipulate the suturing needle 509, or the like. According to certain processes, the operator may be required to hold one or more hands in substantially constant focus of a microscope over prolonged periods of time. Furthermore, the operator may be required to squeeze, push, pull, or otherwise exert manual force on one or more portions of the target implant device 510 and/or suture needle 509.

Figure 6:
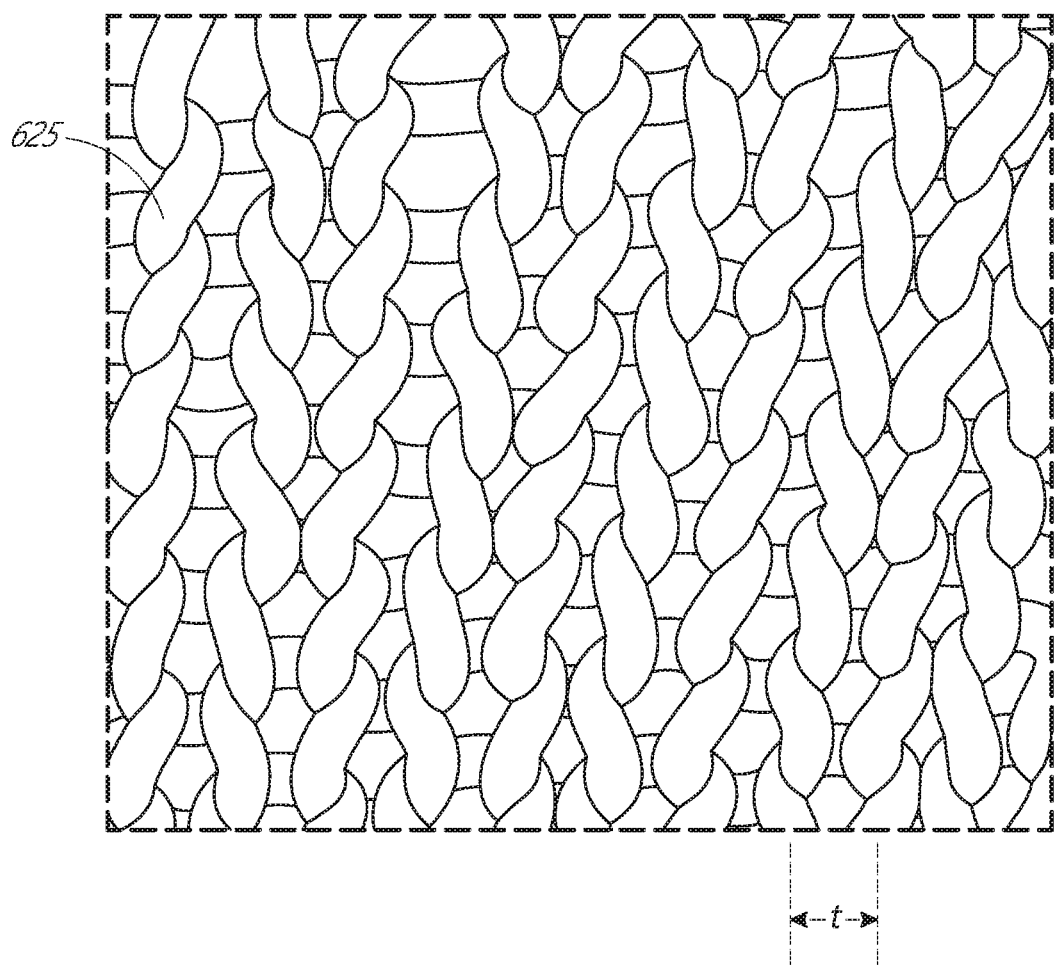
FIG. 6 illustrates a close-up view of a fabric that can be associated with an implant device.

FIG. 6 illustrates a close-up view of a fabric associated with an implant device according to one or more embodiments. Such fabrics may comprise woven strands forming ribs 625 having relatively small gaps therebetween. For example, each rib 625 in a fabric region to be sutured may have a thickness, t, of approximately 0.2 mm or less. For certain processes, one may necessarily or desirably wish to position and sew such a fabric within one-rib accuracy. Thus, precise positioning and focusing of suturing components and targets is desirable.

To address issues identified above and to meet demand for heart valves and other implants, automation of the suturing operation could be beneficial in manufacturing, e.g., to improve manufacturing quality, to improve manufacturing efficiency, to reduce human error, to reduce cost, etc.

Example Automated Suturing Systems with Thread Management

Certain embodiments disclosed herein provide systems and processes for automated suturing of target devices (e.g., prosthetic implant devices or components thereof) using one or more coordinated systems (e.g., target device holders, needle grippers, tensioning devices, thread movement devices, etc.). Such systems can be configured to articulate a target device (e.g., an implant device such as a human prosthetic heart valve device or portion thereof) wherein the precise positioning and orientation of the component or device can allow for necessary or desirable suturing operations performed by an automated sewing or suturing subsystem. Furthermore, the system can be further configured to provide targeted tension to the thread forming the suture during the suturing process. Moreover, the system can be further configured to clear the thread from the path of the needle of the automated suturing subsystem.

Suturing an implant device, heart valve, and/or heart valve component can require suture accuracy within a millimeter, half a millimeter, or less, but a suture location may be easily missed between ribs or threads, particularly due to operator error (e.g., when implementing manual suturing procedures). Embodiments of the present disclosure may improve precision and may help reduce or eliminate human error by using an automated sewing procedure that provides thread management capabilities.

Embodiments disclosed herein provide for systems, devices, and methods for managing thread in an automated suturing system used to suture prosthetic implant devices (e.g., prosthetic heart valves) for humans and/or other types of devices or components. The disclosed systems, devices, and methods can include one or more automated fixtures. For example, a first automated fixture (which can be the same as or similar to the various automated fixtures or automated suture fixtures described and illustrated herein) can be used to articulate and move an implant device to various desired positions and orientations for processing operations or steps (e.g., suturing, treatment, applications, etc.), while a second automated fixture or device could be used to perform the processing operations or steps at the various desired positions (e.g., forming the suture in the target device). As an example, the second automated fixture can be an automated suturing subsystem or device that moves a needle back and forth through a material or surface (e.g., which can be done along a linear path or other suitable path) to add sutures to a target device while the first automated fixture moves the target device to the correct position to receive the desired suture in the correct location on the target device. The disclosed systems can be programmed with a previously specified or defined suturing pattern of an implant or heart valve. Suture tensioning management can also be used to apply and/or to maintain targeted tension on the thread to form sutures. Suture thread management can also be used to clear the needle path of the thread to reduce or eliminate binding or tangling of the thread during the automated suturing process.

In certain implementations, an automated suturing process for one or multiple suturing operations can include two sub-systems or automated fixtures, in which one sub-system or automated fixture is configured to suture or sew the pattern by translating movement of a needle while the other sub-system or automated fixture is coordinated or synchronized therewith and can utilize a multi-axis articulating arm (e.g., a five-axis robotic arm) to grip and move the target implant as desired for suturing. The suturing sub-system or automated fixture can include a thread management device configured to provide a targeted tension on the suture or thread attached to the needle to form the suture and/or to reduce or eliminate problems associated with slack in the suture or thread line (e.g., risk of entanglement, binding, etc.). The implant holding sub-system or automated fixture can include a gripper that does not damage the implant and can be configured to accurately position the target device holder and implant held thereby to receive sutures in targeted locations.

As used herein, the term target device or target suture device includes devices such as the valves 110, 210 and the implant devices 410, 510 and other similar implantable devices. Thus, the automated suturing systems described herein can be used to suture portions of a valve and other similar implant devices or components thereof. The term target device or target suture device may also include any other suitable implant device that includes one or more components that are sutured or sewed.

Figure 7:
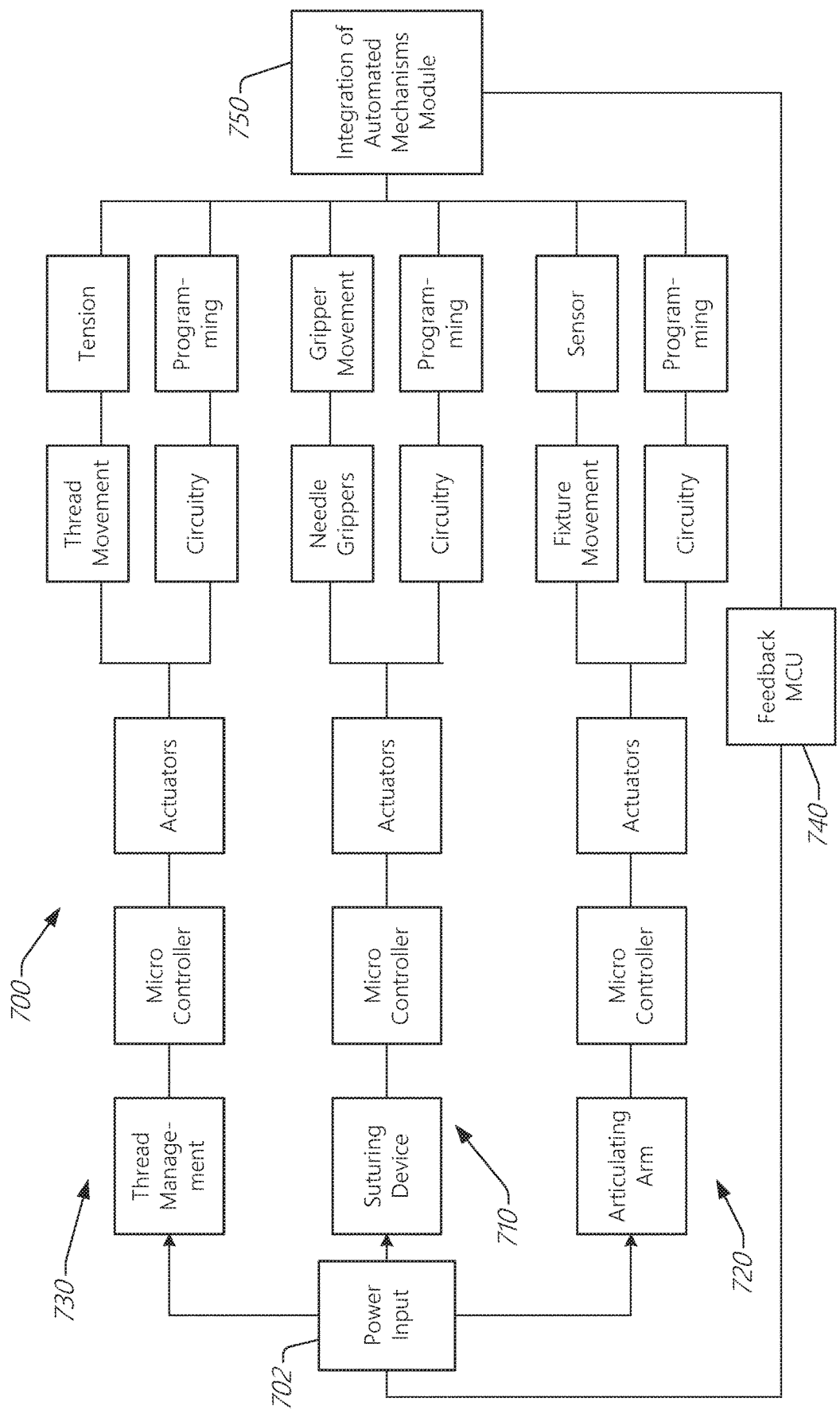
FIG. 7 illustrates a block diagram illustrating an example automated suturing system.

FIG. 7 illustrates a block diagram of an example automated suturing system 700. One or more components of the system 700 can be utilized for suturing heart valve devices or other implant devices, as described herein. The depiction of the system 700 is meant to be illustrative and not limiting, so various components illustrated in FIG. 7 can be omitted from the system 700 and other components not illustrated in FIG. 7 can be added to the system 700.

The system 700 includes one or more power inputs 702, a first automated fixture 710 (e.g., such as a suturing subsystem, suturing device, etc.), a second automated fixture 720 (e.g., such as a movable target device fixture, etc.), a thread management system 730, and a feedback microcontroller unit (MCU) 740, etc. In some embodiments, the power input 702 is outlet power (e.g., of 110 volts) that can be configured to power one or both of the automated fixtures (e.g., one or both of an articulating arm and a suturing subsystem, etc.) and the thread management system 730, but other power inputs are also possible. The system 700 also includes a module 750 to integrate the automated mechanisms 710, 720, 730 based on information or feedback from the feedback MCU 740. The module 750 can include one or more processors, memory, data storage, and the like, such as are typically included in special-purpose or general-purpose computers.

In some implementations, the first automated fixture 710 includes a controller (e.g., microcontroller), one or more actuators, and a suturing device that together are configured to move a needle with thread to form sutures on a target device. The first automated fixture 710 also includes programming, one or more needle holders or needle grippers, circuitry, gripper movement components (e.g., magnetic actuators, pneumatic actuators, linear motion drivers, motors, servo motors, etc.), and/or other components. The first automated fixture 710 uses the actuators, needle grippers, and gripper movement components (e.g., motors, pneumatic actuators, linear motion drivers, and/or servo motors) to move the needle and to coordinate passing the needle back and forth through a surface of the target device in coordination with the second automated fixture 720 to form sutures on the target device.

In some embodiments, the first automated fixture 710 includes two needle grippers. In various implementations, the two needle grippers pass a needle back and forth through a surface of the target device to form the sutures. For example, the two needle grippers can include an inner gripper and an outer gripper that pass the needle from outside the target device to inside the target device and back outside the target device through a material (e.g., a fabric) of the target device to form the sutures. The needle grippers can use any suitable combination of gripper movement components (e.g., magnetic actuators, motors, pneumatics, linear motion drivers, servo motors, etc.) to coordinate movement of the needle grippers back and forth during the suturing process. The programming can be configured to coordinate movement of the needle with processes being run by the second automated fixture 720 and the thread management system 730, the coordination aided by the feedback MCU 740 and/or the integration module 750.

The second automated fixture 720 can include a controller (e.g., microcontroller, etc.), one or more actuators, and an articulating arm that together are configured to position and orient a target device in space for suturing. The second automated fixture 720 also includes fixture movement components (e.g., a fixture gripper, fixture actuators, etc.), programming, circuitry, one or more sensors, and/or other components. The second automated fixture 720 uses the actuators, fixture movement components, and one or more sensors to adjust a position and/or orientation of the target device for each suture in coordination with the first automated fixture 710. The programming can be configured to coordinate movement of the fixture movement components with processes being run by the first automated fixture 710 and the thread management system 730, the coordination aided by the feedback MCU 740 and/or the integration module 750.

The thread management system 730 can include a controller (e.g., microcontroller, etc.), one or more actuators, and a thread management device that together are configured to clear a needle path of the thread and to apply targeted tension to the thread during the suturing process. The thread management system 730 also includes a thread movement device, a tensioning device, circuitry, programming, and/or other components. The thread management system 730 uses the actuators and thread movement device to move the thread during the suturing process so that the thread is out of the path of the needle provided by the first automated fixture 710. The thread management system 730 uses the actuators and tensioning device to provide a targeted tension during the suturing process, where the targeted tension can change at various points in the process. In some embodiments, the thread movement device and the tensioning device can be integrated into a single device.

The first automated fixture 710, the second automated fixture 720, and the thread management system 730 can be integrated and synchronized to form sutures on a target device. To form sutures on the target device, the first automated fixture 710 (e.g., suturing device) coordinates movement of needle grippers to pass a needle with thread back and forth through a surface of a target device that is held and moved into desired positions by the second automated fixture 720 (e.g., a multi-axis robotic arm, articulating fixture, other fixture, etc.) while the thread management system 730 provides tension on the thread and clears the needle path of the thread.

In some embodiments, the system 700 and/or one or more of the automated fixtures includes one or more controllers (e.g., microcontrollers, etc.) configured to direct one or more components of the automated fixtures and/or other components according to a predefined or programmed suturing process. The controller(s) can comprise one or more hardware and/or software components designed to generate and/or provide fixture control signals (e.g., suture fixture control signals) and/or data associated with one or more steps of a suturing process. For example, the controller(s) can comprise a computing device including one or more processors, as well as one or more data storage devices or components, which can include volatile and/or nonvolatile data storage media. In certain embodiments, the data storage is configured to store process script data (e.g., suture process script data), which can comprise data indicating positioning of one or more components and/or fixtures of the system 700 for various steps and/or stages of the suturing process. A process comprising a plurality of steps can be represented at least in part by numeric or other data sets representing positioning information for one or more components of the automated fixtures and/or one or more additional components of the system 700 for each respective step or stage of the process. For example, a suturing process comprising a plurality of suturing steps can be represented at least in part by numeric or other data sets representing positioning information for one or more components and/or fixtures of the system of the system 700 for each respective step or stage of the suturing process.

The first automated fixture 710 can be configured to manipulate a needle. Various needles can be used. In some implementations, a non-corrosive dual-sided needle comprising one or more of NiTi/Nitinol, Delrin, cobalt chromium, ABS plastic, PEEK plastic, strong plastic having a polycarbonate base is used. The needle can be double-sided with an eye near a middle of the needle through which the thread passes with both ends of the needle being configured to penetrate fabric or other material (e.g., a cover, seal, leaflet, or the like) being sewn to a stent or frame of the target device. Advantageously, this allows the first automated fixture 710 to pass the needle back and forth through a surface of the target device without needing to rotate the needle between stitches or sutures. However, a single-sided needle may also be used. Such a needle can include an eye opposite the penetrating end of the needle or between the end and another point along the needle, e.g., the middle of the needle.

The first automated fixture 710 comprises needle holders (e.g., needle grippers or needle gripping mechanisms) configured to hold the needle during the suturing process. The needle holders or grippers can be configured in a variety of ways. For example, the needle grippers can grip the needle in a way that is similar to a drill chuck tool-holder or any of a variety of mechanical methods. Other examples of gripping mechanisms include magnetism, pneumatics, hydraulics, vacuum pressure, and the like.

In some embodiments, the second automated fixture 720 comprises one or more components configured to articulate, rotate, operate, and/or position one or more actuators to present a target device (e.g., a heart valve, implant, or other suture target) in a desirable or suitable position or presentation for engagement or interaction therewith by another fixture executing at least part of a process (e.g., a suturing process). In some embodiments, the second automated fixture 720 can be configured to provide limited movement, such as rotation without translation or rotation in combination with translation along a single axis. In some embodiments, the second automated fixture 720 can be configured to provide a wide range of motion, such as rotation about a plurality of axes and movement along a plurality of axes (e.g., two or three axes or more).

In some embodiments, the second automated fixture 720 includes a plurality of actuators that are mounted, attached, or connected to one another in a configuration that provides a desirable range of motion for a target device (e.g., a suture target) associated with or held by the automated fixture. In certain embodiments, a target holder component or assembly can be associated with, or connected to, one or more of the actuators. The actuators can each comprise one or more rotating or otherwise articulating members driven by motors, pneumatics, magnets, drivers, or the like.

The second automated fixture 720 can include a holder or holder assembly (e.g., a gripper or gripping fixture) configured to hold the target device while sewing occurs. For example, a holder formed as a gripper can be a multi-prong gripper (e.g., a two or a three-prong gripper) configured to hold the target device while sewing occurs. Other examples of the gripper include, but are not limited to, an inside-bellow gripper, a pronged gripper, a 3-D printed gripper, a caged gripper, or another type of gripper. In some embodiments, a target holder assembly configured to hold or secure the target device (e.g., the prosthetic implant device) can be similar to the target holder assembly illustrated in FIG. 13.

The first automated fixture 710, the second automated fixture 720, and/or the thread management system 730 can also include various sensors such as a vision camera or the like. For example, the second automated fixture 720 can include sensors to detect the position and orientation of the target holder during the suturing or sewing process and/or sensors to detect forces involved in the process. For example, the second automated fixture 720 can also include a gripping force sensor, which can be configured to relay the force that the gripper exerts on the target device. The second automated fixture 720 can also include a gyroscope sensor, which can be configured to measure the rotation of the second automated fixture 720, an end actuator thereof, an articulation arm thereof, a fixture holder thereof, or the like. The second automated fixture 720 can also include an accelerometer sensor, which can be configured to measure the position of the automated fixture 720, an end actuator thereof, an articulation arm thereof, a fixture holder thereof, or the like. The thread management system 730 can include one or more sensors to determine positions and/or orientations of various components and/or to determine forces or tensions applied to the thread.

In some embodiments, the second automated fixture 720 is configured to move, rotate, etc. the target device as the first automated fixture 710 moves the needle along a fixed path to create a desired suture pattern. The movement of the target device can occur in three spatial dimensions and can also include rotational movement about any axis or combination of axes of the three spatial dimensions. The automated fixtures 710, 720 and the thread management system 730 can be programmed, coordinated, or synchronized to work together to accomplish a variety of desired suture patterns on a variety of implants. Coordination can be accomplished using the integration module 750 in conjunction with the feedback MCU 740.

In certain embodiments, the automated fixtures 710, 720 and/or the thread management system 730 (collectively referred to as automated suture fixtures) comprise one or a plurality of actuators (e.g., servo actuators, motors, magnetic actuators, drivers, pneumatics, etc.) physically coupled to one another. By constructing the automated suture fixtures 710, 720, 730 using one or a plurality of actuators devices (e.g., servo motor components), the system 700 may be relatively inexpensive and/or advantageously provide an enhanced range of motion, as well as multiple axes of rotation. In certain embodiments, one or more of the automated suture fixtures 710, 720, 730 comprises a plurality of actuator devices (e.g., servo actuator devices) daisy-chained together and implemented using a software script to provide cooperative functionality for the purpose positioning the target implant device. For example, the actuator devices or servo actuator devices (e.g., servo motor devices) can be mounted, or configured to be mounted, horizontally or vertically or at an angle, and can be articulated in any direction.

In certain embodiments, the microcontrollers provide control signals for directing the positioning and/or operation of the automated suture fixtures 710, 720, 730 (or actuators of the fixtures) based on a positioning script, suture process script, and/or user input provided by an operator. For example, the system 700 (or a system 1700 described herein with reference to FIG. 12) can include a user input device (not shown), which can be used by an operator to provide input initiating or directing the operation of the controller and/or automated suture fixture assembly. For example, the user input device can comprise any suitable user input interface, such as a mechanism for user input in connection with a graphic user interface associated with an electronic display, wherein an operator can provide input through interaction with the interface.

In certain embodiments, the actuator devices are implemented using piezoelectric control with analog voltage signals. In certain embodiments, one or more components of the automated suture fixtures 710, 720, 730 are controlled using pulse width modulation control signals, such as control signals spaced by between 0 to 2 µs, for example. In certain embodiments, multiple actuator components (e.g., multiple servo motor components) of the automated suture fixtures 710, 720, 730 share one or more common leads with a multiplex signal, such as a three-lead connection. In certain embodiments, the automated suture fixtures 710, 720, 730 comprise four or five or more actuator devices. Devices and fixtures disclosed herein can be remote-controllable or partially remote-controllable.

Example Automated Suturing Systems with Thread Management

Figure 8:
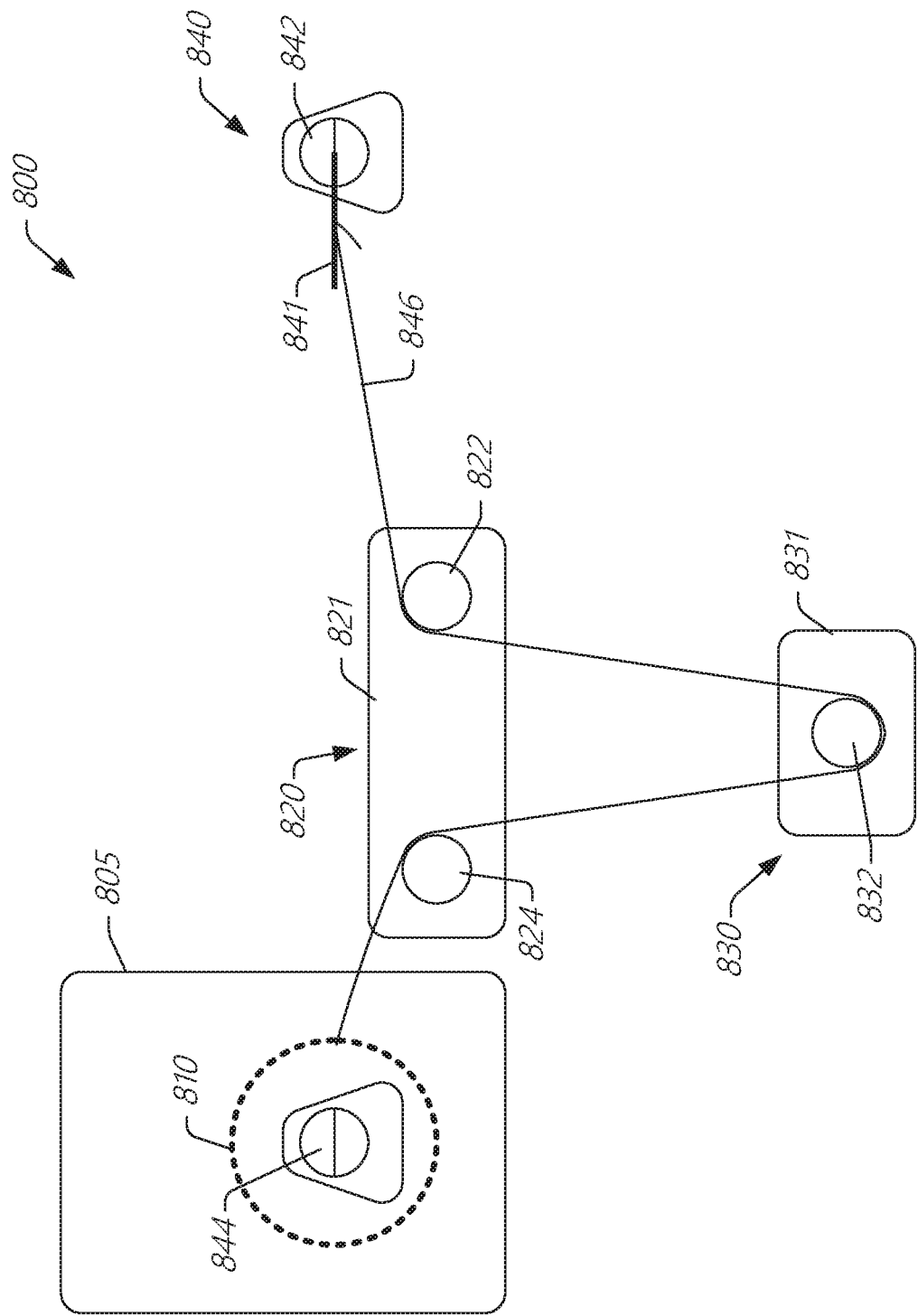
FIG. 8 illustrates an example embodiment of an automated suturing system with an automated thread management system.

FIG. 8 illustrates an example embodiment of an automated suturing system 800 with an automated thread management system. The thread management system includes a thread support component 820 and a tensioning component 830. The suturing system 800 also includes a sewing apparatus 840 and an automated fixture holder 805 of an automated fixture configured to hold and manipulate a target device 810. The suturing system 800 is configured to coordinate movement of its various components (including the thread management system, the sewing apparatus 840, and the fixture holder 805) to form stitches at targeted locations on the target device 810 while avoiding entanglement or binding of a thread 846 being used to form the stitches.

The thread support component 820 includes a support bracket 821 and support pins 822, 824 coupled to the support bracket 821. The support pins 822, 824 are configured to support the thread 846 being used to form stitches on the target device 810 during various phases of the suturing process (e.g., during tensioning of the thread). The tensioning component 830 includes a tension bracket 831 and a tensioning pin 832 secured to the tension bracket 831. The tensioning pin 832 is configured to apply tension to the thread 846 being used to form stitches on the target device 810 during various phases of the suturing process. As described herein, the thread movement component 820 can also configured to adjust the direction of the tension on the thread 846.

Figure 9A:
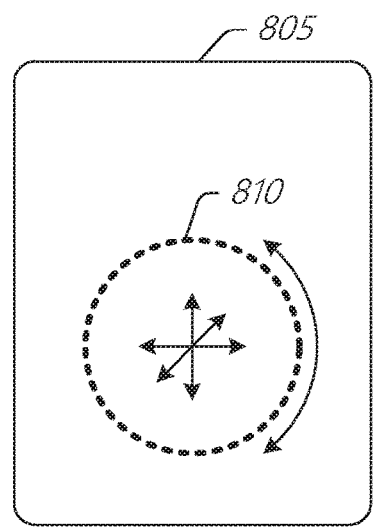
FIG. 9A illustrates functionality of the automated fixture holder of the automated suturing system of FIG. 8.

FIG. 9A illustrates functionality of an automated fixture holder 805 of an automated fixture of an automated suturing system, such as in automated suturing system 800 of FIG. 8. The automated fixture holder 805 is configured to move and orient the target device 810. The automated fixture holder 805 is configured to move the target device 810 in a number degrees of freedom. This can include, for example, positioning in one or more (e.g., all) of the three spatial dimensions, rotation, and/or rotation around a longitudinal axis of the target device 810 (e.g., keeping the position and pointing direction of the target device 810 fixed while rotating the target device 810 around its longitudinal axis).

Figure 9B:
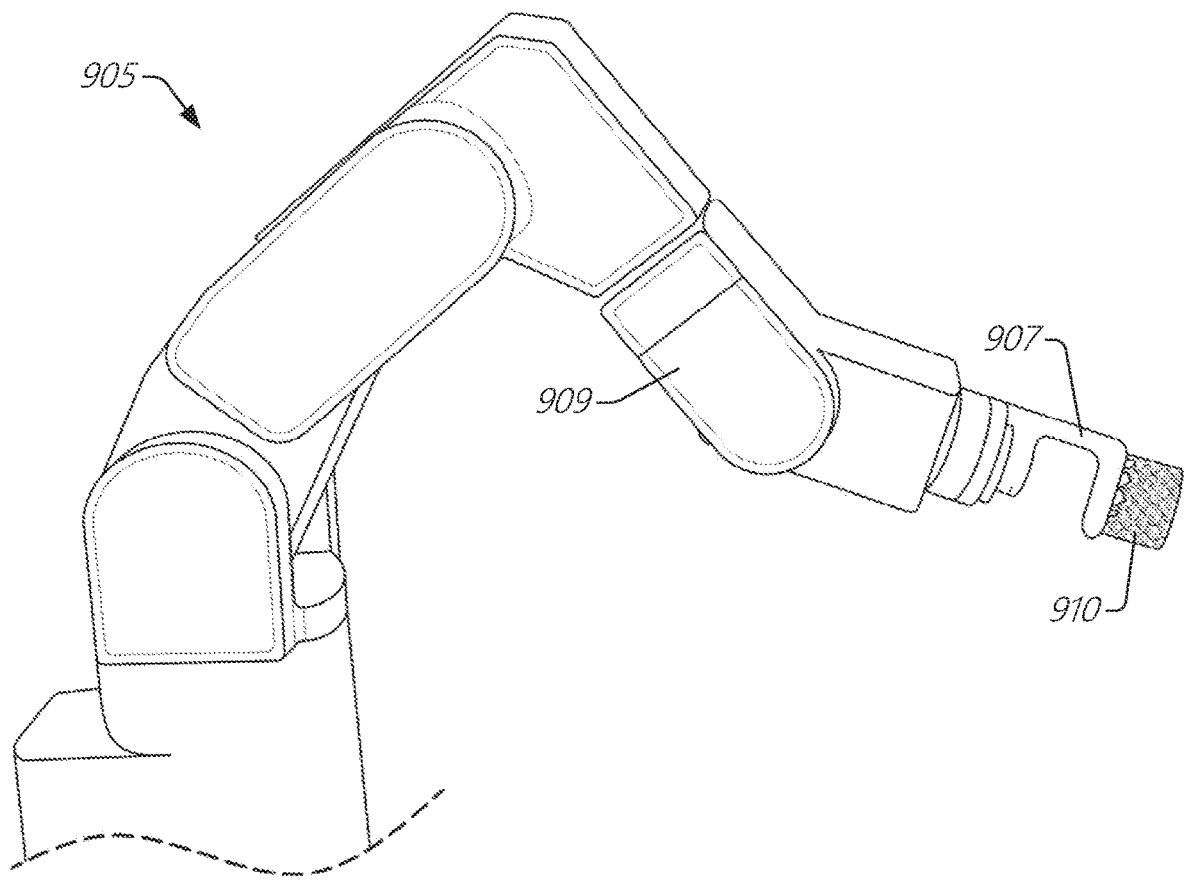
FIG. 9B illustrates an example automated fixture holder having an articulation arm and a target device holder.

FIG. 9B illustrates an example automated fixture and/or automated fixture holder 905 having an articulation arm 909 and a target device holder 907. The articulation arm 909 has a crane-like configuration and is configured to substantially enclose a plurality of actuation devices within a housing or a plurality of housings. The articulation arm 909 secures a target assembly 907 that is configured to secure a target device 910 such as a heart valve implant. The articulation arm 909 can be configured to move and to manipulate the target assembly 907 which in turn moves and orients the target device 910. The combination of the articulation arm 909 and the target assembly 907 move the target device 910 in any of the three spatial dimensions (e.g., movement in the x-axis, y-axis, and z-axis; horizontal movement, vertical movement, or a combination of horizontal and vertical movement), rotate the target device 910 (e.g., rotation about the x-axis, about the y-axis, and/or about the z-axis), and/or rotate the target assembly 907 around a longitudinal axis of the target device 910 (e.g., keeping the position and pointing direction of the target device 910 fixed while rotating the target device 910 around its longitudinal axis).

Figure 10A:
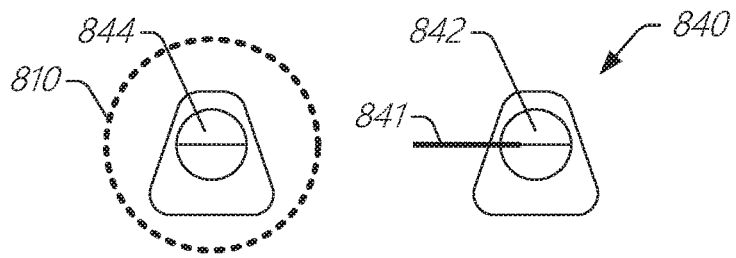
Figure 10B:
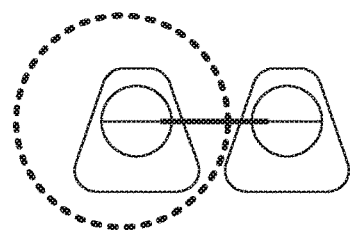
Figure 10C:
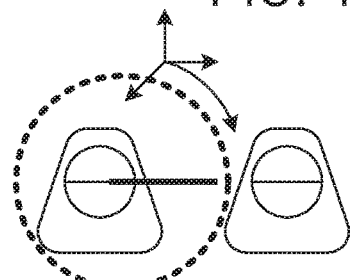
Figure 10D:
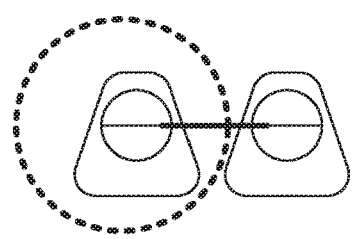
Figure 10E:
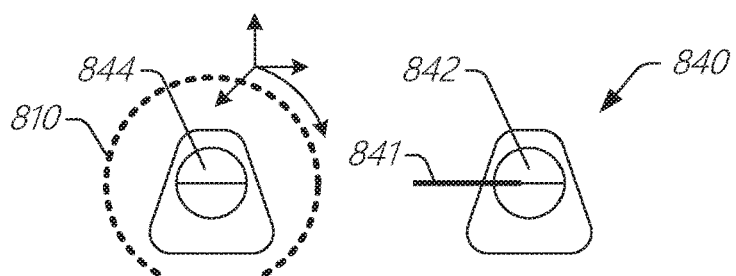

FIGS. 10A-10E illustrate an example suturing process as performed by the automated fixture and/or sewing apparatus 840 of the automated suturing system 800 of FIG. 8. The figures illustrate the process using a simplified view of the system 800 and associated components for simplicity and clarity. The sewing apparatus 840 includes a first or outer needle gripper 842 and a second or inner needle gripper 844 that are configured to pass a needle 841 back and forth through a surface of the target device 810. The outer needle gripper 842 traverses a fixed linear path outside of the target device 810, approaching the target device as illustrated in FIG. 10A. The outer needle gripper 842 moves toward the target device 810 causing the needle to penetrate through a surface of the target device 810 where it is received by the inner needle gripper 844, as illustrated in FIG. 10B. The inner needle gripper 844 moves the needle 841 inward so that the needle 841 entirely passes through the surface of the target device 810, at which point the target device 810 is rotated or otherwise moved, as illustrated in FIG. 10O. After the target device 810 is adjusted to its next position, the inner needle gripper 844 passes the needle 841 back through the surface of the target device 810 where it is received by the outer needle gripper 842, as illustrated in FIG. 10D. The outer needle gripper 842 then returns to its original starting location in preparation for the next stitch, as illustrated in FIG. 10E. Prior to forming the next stitch, the target device 810 can be moved and/or rotated again so that the fixed path of the needle 841 intersects the surface of the target device 810 at the location of the next stitch, as illustrated in FIG. 10E.

As used herein, the term "stitch," referring to a single stitch, is formed by passing the needle 841 with the thread 846 through the surface of the target device 810 two times. For example, where the target device 810 is generally cylindrical, a single stitch is formed by passing the needle 841 from outside the target device 810 to inside the target device 810 through its surface, and back from the inside to the outside of the target device 810. It should also be understood that the target device 810 need not have an inside or an outside and that, in such instances, a single stitch is formed by passing the needle 841 through a surface of the target device 810 from a first side to a second side and back through the surface to the first side.

Returning to FIG. 8, forming a stitch includes using the needle grippers 842, 844 to cause the needle 841 to traverse a fixed needle path to form stitches on the target device 810. The thread management system is configured to move the thread 846 coupled to the needle 841 out of the needle path and to apply tension to the thread 846. The automated fixture holder 805 is configured to adjust a position and/or orientation of the target device 810 so that the needle 841 is passed through targeted locations of the target device 810 as the needle 841 traverses the fixed needle path.

Tension is applied to the thread 846 using a combination of the tensioning pin 832 and the support pins 822, 824. As an example, the tensioning pin 832 can push downward on the thread 846 and the support pins 822, 824 redirect the path of the thread 846 from the needle 841 to the target device 810. The tension can be configured to be sufficient to hold down the previous suture and to maintain the thread 846 out of the needle path. This way, entanglement of the thread 846 with the needle 841 can be avoided or eliminated.

In some embodiments, the support pins 822, 824 can be positioned to provide a targeted directionality for the tension on the thread 846. For example, the support pin 824 can be configured so that, as tension is applied by the tensioning pin 832, the support pin 824 supports the thread 846 so that it is pulled in a direction substantially orthogonal to the surface of the target device 810 where the stitch is being formed. In certain implementations, the support pins 822, 824 can be positioned so that application of tension to the thread 846 causes a substantially horizontal force (e.g., reducing or eliminating vertical forces) on the needle 841 and the target device 810 (e.g., by pulling on the newly formed stitch). Advantageously, the directionality of the tension can be configured to reduce bending or deforming the needle 841 as it is gripped by the outer needle gripper or to reduce the likelihood the needle 841 is moved or dislodged from the outer needle gripper. Similarly, this can be advantageous to reduce deforming the fabric or stent of the target device 810, to reduce the likelihood of moving or dislodging the target device 810 in the target holder, to reduce unwanted increasing space between ribs of a fabric of the target device 810 (e.g., creating a hole in the material), or otherwise damaging the target device 810.

In certain embodiments, the thread 846 can be released from one or more of the support pins 822, 824 or tensioning pin 832 during one or more portions of forming the stitch. Releasing the thread 846 during the process of forming the stitch can aid in reducing or eliminating entanglement of the thread 846. During formation of the stitch, the tensioning pin 832 can be configured to move the thread 846 in a direction substantially orthogonal to the needle path to clear the needle path, to apply tension to the thread 846, and/or to pull a slack portion of the thread 846 through the surface of the target device 810. For example, tensioning the thread 846 pulls the slack portion of the thread 846 through the surface (e.g., fabric) of the target device 810 to finalize a newly formed stitch.

Figure 11A:
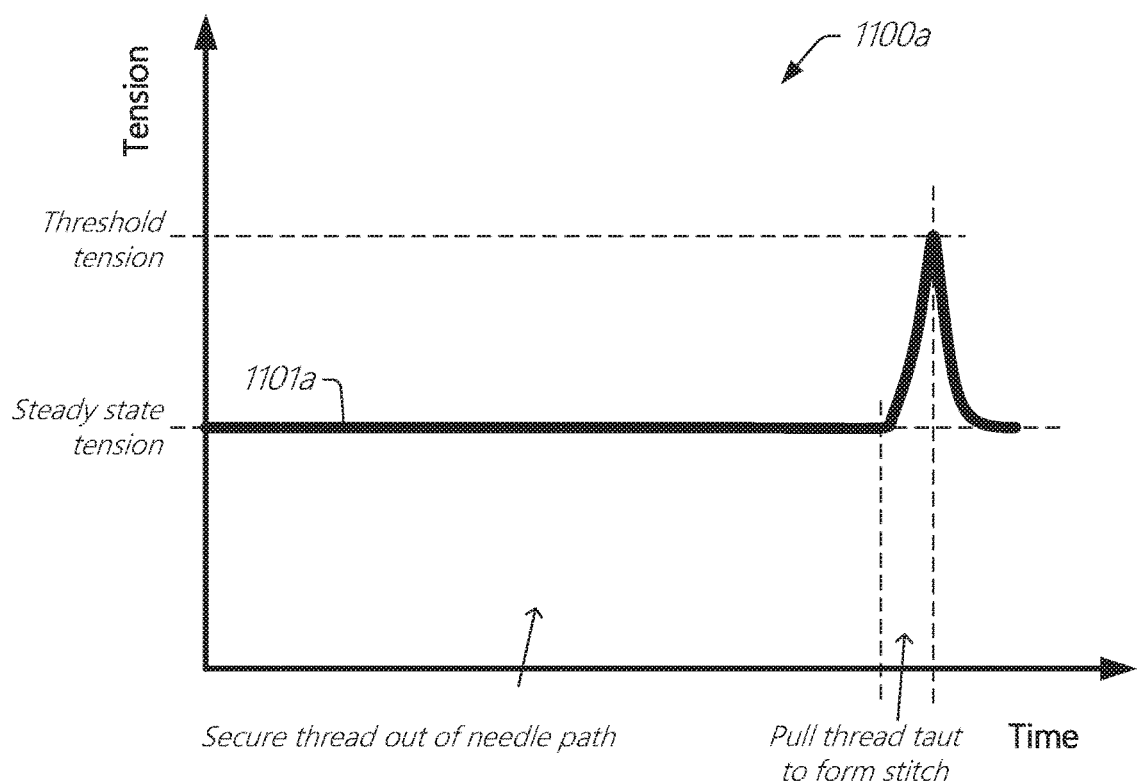
FIGS. 11A and 11B illustrate examples of tension on a thread where the tension varies over time.
Figure 11B:
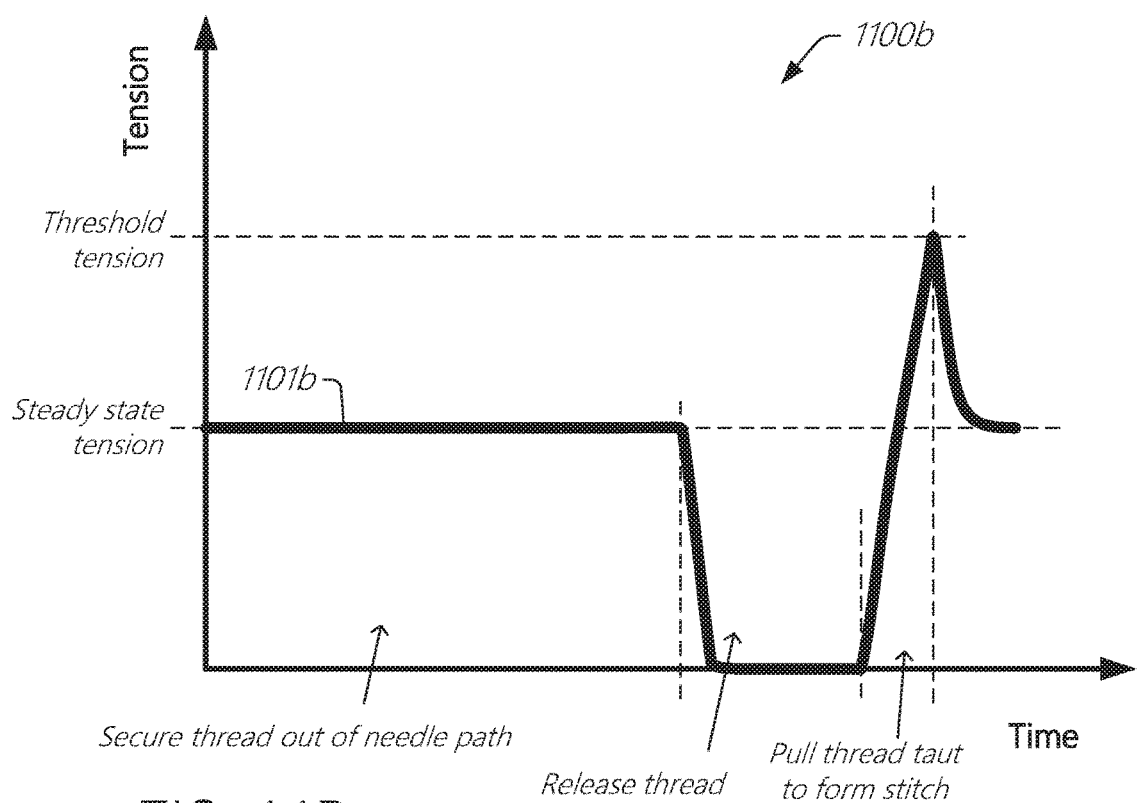

In some embodiments, different tensions can be applied at different points in the process of forming a single stitch. FIGS. 11A and 11B illustrates example graphs 1100a, 1100b of tension 1101a, 1101b applied over the process of forming a single stitch. This process can be repeated to form multiple stitches on the target device 810.

In the graph 1100a of FIG. 11A, the tension 1101a applied to the thread can be a steady state tension during a portion of the stitch formation process where the steady state tension is configured to hold the stitch in place and to maintain the thread clear of the needle path. Between finalizing the stitch and beginning a new stitch, the tension applied to the thread can at least temporarily exceed the steady state tension. For example, tension can be applied to the thread that increases until it reaches a threshold tension that is greater than the steady state tension. Once the threshold tension is reached, the tension is reduced to the steady state tension. The threshold tension is configured to be large enough to pull the thread to finalize the stitch, pulling through any potential snags or entanglements in the thread, so that the finalized stitch is flush with the surface (e.g., a fabric or other material) of the target device. The steady state tension is configured to maintain the stitch in a held down state so that the next penetration of the needle does not also penetrate the previous stitch. The steady state tension can be less than the threshold tension to reduce strain on the needle, the needle grippers, the target device, and/or the fixture holder. In some embodiments, the tension threshold is at least about 35 g (or about 0.34 N) and/or less than or equal to about 50 g (or about 0.49 N), for example about 40 g (or about 0.39 N). In some embodiments, the steady state tension is at least about 20 g (or about 0.2 N) and/or less than or equal to about 35 g (or about 0.34 N), for example about 29 g (or about 0.28 N).

The graph 1100b of FIG. 11B illustrates that, in some embodiments, the tension 1101b on the thread can be released during a portion of the stitch formation process. As in the graph 1100a, a steady state tension can be applied to the thread to secure the thread out of the needle path. This can be done when the needle is passed from a first side to a second side of the target device through a surface of the target device. When the needle is passed from the second side back to the first side, tension can be released to allow the needle to return to its starting position and/or to reset the tensioning and thread positioning components. Tension can then be reapplied, up to a threshold tension, to pull the remaining slack thread through the surface of the target device to form the stitch. Once the threshold tension is achieved, the tension can return to the steady state tension to hold the stitch in place as the process is begun again to form a new stitch. As described herein, the threshold tension can be configured to be high enough to prevent or reduce binding or entanglement of the thread as it is pulled through the surface of the target device and to finalize the stitch. The steady state tension can be configured to be sufficient to hold down the formed stitch during the suturing process.

Example Control System for Automated Suturing System

Figure 12:
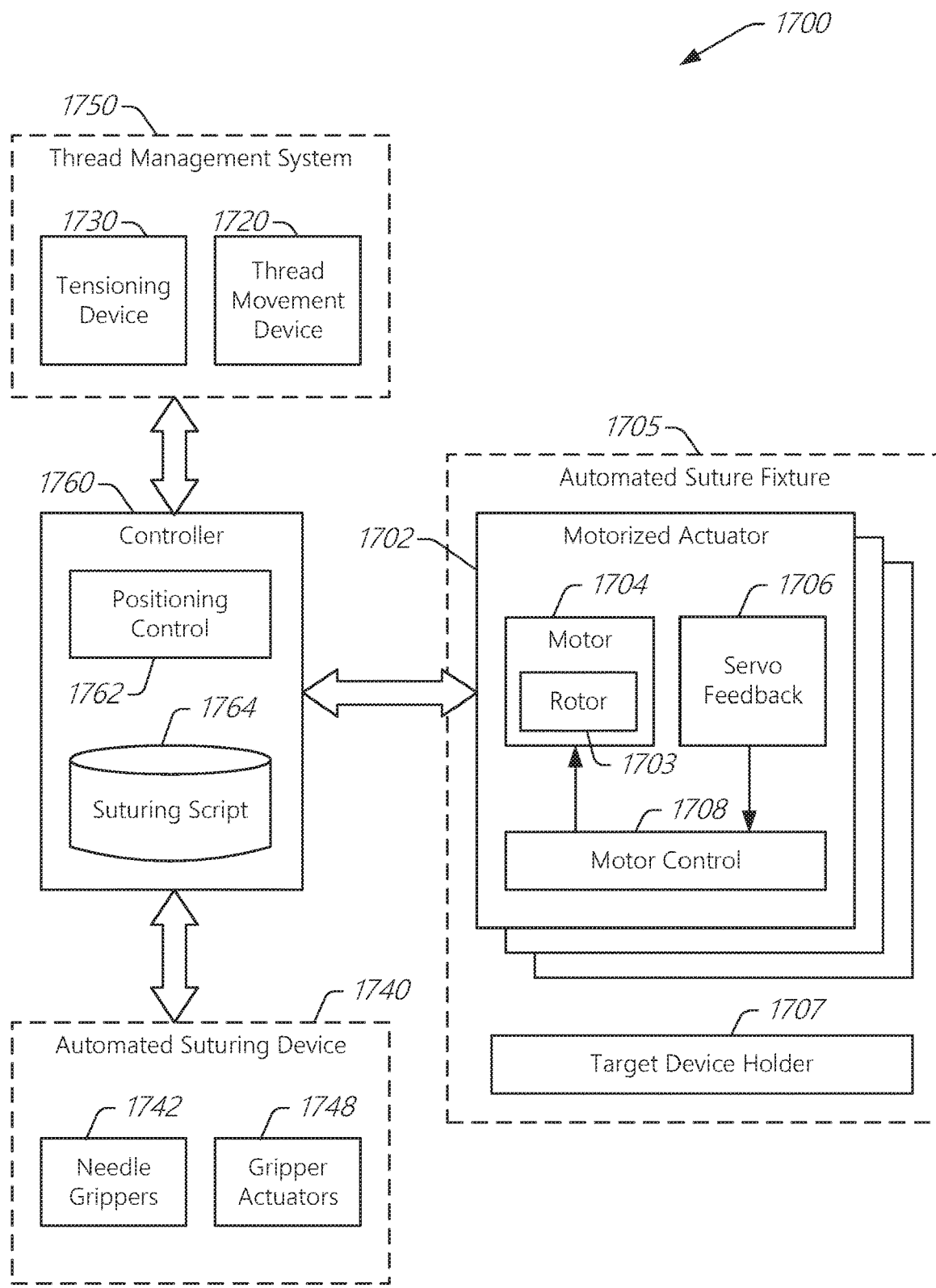
FIG. 12 illustrates a block diagram of an example control system for controlling an automated suturing system.

FIG. 12 illustrates a block diagram of an example control system 1760 for controlling an automated suturing system 1700. The automated suturing system 1700 can include a variety of components, features, systems, automated fixtures, combinations of these, etc. In some implementations, the automated suturing system 1700 includes a first automated fixture or an automated suturing device 1740, a second automated fixture or automated suture fixture 1705, and a thread management system 1750. Additional automated fixtures could also be used. Also, the systems herein can include multiple combinations of the components and fixtures, for example, to simultaneously control and operate multiple suturing operations on multiple target devices.

The controller 1760, also referred to as control system 1760, can provide input to the various components and devices and receive feedback from these components and devices to coordinate operation of the automated suturing system 1700.

The first automated fixture or automated suturing device 1740 is configured to manipulate a needle to form stitches on the target device. The second automated fixture or automated suture fixture 1705 is configured to articulate a target device (e.g., prosthetic human heart valve implant) to a desired suture position. The thread management system 1750 is configured to move the thread out of the needle path and apply tension to the thread.

The first automated fixture or automated suturing device 1740 (which can represent any or all of the automated suturing devices described herein), the second automated fixture or automated suture fixture 1705 (which can represent and be the same as or similar to any or all of the automated fixtures that move a target device described herein), and the thread management system 1750 (which can represent and be the same as or similar to any or all of the thread management systems described herein) are each configured to receive control signals from the controller module 1760. The controller module 1760 can comprise a combination of software and/or hardware components configured to generate control signals for at least partially directing the operation of the automated suture fixture 1705, the automated suturing device 1740, the thread management system 1750, and/or one or more components thereof.

In certain embodiments, the controller 1760 includes one or more processors and/or controller circuitry configured to access suturing script information 1764 or other script or program information maintained by the controller in data storage thereof, or otherwise accessed by the controller 1760. The controller 1760 can include positioning control circuitry 1762 designed to interpret suturing script information or other script or program information and to generate control signals for controlling the first automated fixture or automated suturing device 1740, the second automated fixture or automated suture fixture 1705, and the thread management system 1750 based at least in part thereon.

The suturing script information 1764 or other script or program information can comprise sequential positioning information for one or more components of the automated fixtures (e.g., automated suture fixture(s) 1705, the automated suturing device 1740, and/or any additional automated fixtures used) and the thread management system 1750 with respect to one or more suturing processes or other processes that the controller 1760 is designed to implement. For example, in some embodiments, the positioning control circuitry 1762 is configured to provide position information for each step of a suturing process in sequence. The advancement from one position step to another can be directed by the controller 1760 based on a timer, feedback from one or more components, and/or user input.

The automated suture fixture 1705 can include a plurality of motorized actuators 1702, which can be communicatively coupled to the controller 1760. In certain embodiments, the motorized actuators 1702 are coupled to one another in a daisy-chain configuration, wherein two or more of the motorized actuators are coupled or wired together in sequence. Although motorized actuators 1702 are described in detail with respect to FIG. 12, it should be understood that any suitable combination of actuators and/or drivers may be used with the automated suture fixture 1705 and, relatedly, the automated suturing device 1740 and the thread management system 1750.

Each of the motorized actuators 1702 can include a motor 1704, such as a DC, AC, or brushless DC motor. The motor 1704 can be a servo motor. In certain embodiments, the motor 1704 is controlled using pulse-coded modulation (PCM), as directed by motor control circuitry 1708. For example, the motor control circuitry 1708 can apply a pulse application for a certain period of time, wherein the angular positioning of a rotor component 1703 is determined at least in part by the length of the pulses. The amount of power applied to the motor 1704 can be proportional to the rotational distance of the rotor 1703.

In certain embodiments, the motorized actuators 1702 are servo actuator devices including one or more servo feedback component(s) 1706, such as a position sensor (e.g., a digital encoder, magnetic encoder, laser(s), etc.). Use of servo feedback component(s) 1706 may be desirable in order to achieve a desirable level of confidence that the motorized actuators 1702 are positioned as directed by the controller 1760 with an acceptable degree of accuracy. The servo feedback component(s) 1706 can provide a signal (e.g., an analog or digital signal) to the motor control circuitry 1708 indicating a position and/or speed of the rotor 1703, which may advantageously allow for relatively precise control of position for faster achievement of a stable and accurate rotor position. Relatively accurate positioning of an implant device may be necessary or desirable due at least in part to the dimensions of the material or cloth of a heart valve or other implant device that is sutured in an implant suturing operation using the automated suture fixture 1705. For example, the fabric or other material being sutured can comprise woven strands forming ribs having relatively small gaps therebetween. In certain embodiments, the automated suture fixture 1705 can be configured to articulate a suture target prosthetic human implant device within 0.2 mm accuracy, and others can operate with greater or less accuracy than this. Although servo motor devices and components are described, in some embodiments, one or more motorized actuators can comprise stepper motors, or other types of motor subsystems.

The motorized actuators 1702 can include motor control circuitry 1708, which can drive the motor 1704 according to the control signals received from the controller 1760. In certain embodiments, the motor 1704, in combination with the servo feedback mechanism 1706 and/or motor control circuitry 1708, can advantageously be configured to retain the rotor 1703 and/or attached support member in a set position for desired periods of time. The motor 1704 can provide relatively smooth commutation and/or accurate positioning of the associated rotor 1703. The motor 1704 can be relatively powerful relative to its size and may draw power proportional to the mechanical load present on the rotor 1703 and/or associated support member.

In some embodiments, the servo feedback component 1706 comprises a potentiometer that is connected to the rotor 1703, which can be the output device of the motorized actuator 1702. The rotor 1703 can link to the potentiometer and control circuitry 1708, wherein the potentiometer, coupled with signals from the control circuitry, controls the angle of the rotor 1703 (and associated support member) across a rotational range, such as between 0°-180°, or further. In certain embodiments, the rotational range of the rotor 1703 is restricted by one or more mechanical stops, which can be built into associated gear mechanism(s). The potentiometer (or other servo mechanism, such as an internal rotary encoder) can allow the control circuitry 1708 to monitor the current angle of the motor or rotor. When the rotor 1703 is at the correct angle, the motor 1704 can idle until the next positioning signal is received from the controller 1760.

The automated suture fixture 1705 can further include a suture target holder device or assembly 1707 (while called a suture target holder or assembly herein, this can be another type of target holder device, gripper, or assembly to hold target devices or components for other procedures). The suture target holder 1707 can be physically coupled to one of the motorized actuators 1702, such as to distal extension arm actuator device of the plurality of actuators. The suture target holder 1707 can be configured to hold or have mounted thereto a prosthetic heart valve device, or other prosthetic human implant device, which is desired to be sutured. The suture target holder 1707 can have any suitable or desirable shape, configuration and/or dimensions and can be configured to hold or secure a target device or implant device in a variety of different ways. An example embodiment of a suture target holder device or assembly is described herein with reference to FIG. 13. However, it should be understood that such an embodiment is provided merely as an example, and other types of suture target holders can be implemented in the disclosed systems.

Figure 13:
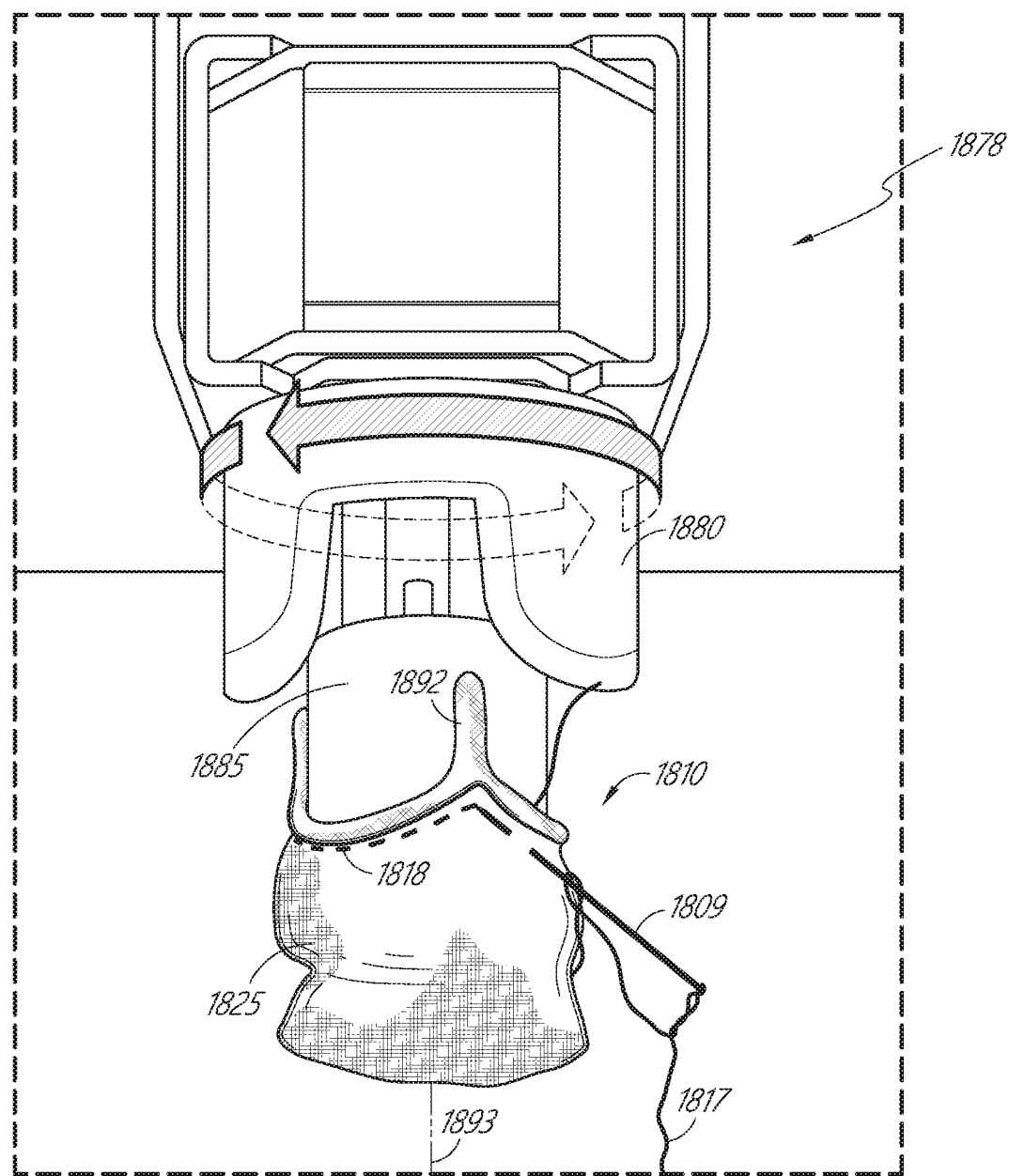
FIG. 13 illustrates a distal portion of an articulation arm of an automated fixture holder with a target device secured to a target device holder.

FIG. 13 illustrates a distal portion of an articulation arm 1878 of an automated fixture holder 1878 with a target device 1810 secured to a target device holder 1880. The articulation arm 1878 can include one or more actuators coupled to the holder component 1880. In certain embodiments, a holder component 1880 is fixed or secured to the distal articulation arm 1878 or end actuator of an automated suture fixture for the purpose of providing an interface for securing an implant device or other target form or device. The holder component or assembly 1880 can be designed or configured to hold or secure an implant device or other target device, or portion thereof, for the purpose of allowing suturing thereof according to any process or embodiment disclosed herein. The holder component 1880 can be configured to secure or otherwise include a cylinder form 1885, which can be sized or dimensioned to have pulled thereover the target device or implant (e.g., a fabric-covered support stent for a surgical valve implant device 1810). For example, the valve implant device 1810 can comprise a plurality of commissure post portions 1892, as illustrated, which can be positioned such that they are oriented in a direction towards the holder component 1880, such that a seam 1818 can be stitched above what will ultimately represent an inflow edge of the implant device 1810. The cylindrical form or component 1885 can be designed in a similar manner to a handheld implant device holder, which can be used in certain embodiments in executing suturing procedures without the assistance of the articulation arm 1878 and associated components. The cloth 1825 can be disposed about a rigid wireframe structure, wherein the seam of stitches 1818 is executed in order to substantially cover the wireframe with the cloth 1825. The seam 1818 can secure the cloth 1825 about a stiffening band, as illustrated in FIG. 3A and described.

The holder component 1880 can be designed for a particular application, such as for a transcatheter heart valve suturing application, or a surgical heart valve suturing operation, or other implant suturing procedure. The valves can be for animal (e.g., for human) use. Although a surgical valve configuration is illustrated in FIG. 13, it should be understood that the holder device 1880 and/or other components of FIG. 13 can be designed or configured to support suturing processes and/or other processes for a transcatheter heart valve or other valve or other device. For example, although the diagram of FIG. 13 illustrates a cylindrical form 1885 designed to hold the implant device 1810 in a desired position, such cylindrical form may not be necessary with respect to a transcatheter heart valve. For example, in place of the cylindrical form 1885, the holder 1880 can instead be configured to secure a rigid cylindrical wireframe of a transcatheter heart valve, an embodiment of which is illustrated and described above in connection with FIG. 1.

The specific type of holder that is utilized for a procedure or application (e.g., for a suture assist application) can be determined on a process-by-process basis. That is, specific adapters may be suitable or desirable for each of separate operations or procedures, or for separate types of valves or other targets. In certain embodiments, a single suturing procedure of an implant device can involve use of multiple different types of holder devices.

Returning to FIG. 12, the automated suturing device 1740 includes one or more needle grippers 1742 with corresponding gripper actuators 1748. The needle grippers 1742 can be configured to secure and to release a needle during a suturing process. The gripper actuators 1748 can be configured to move the needle grippers 1742 according to the suturing process. The controller 1760 can provide the automated suturing device 1740 control signals to coordinate operation of the needle grippers 1742 and gripper actuators 1748 with the automated suture fixture 1705 and the thread management system 1750. The gripper actuators 1748 can operate in a manner similar to the motorized actuators 1702 and/or motors 1704 of the automated suture fixture 1705, and the description of these components as well as the rotor, servo feedback, and motor control circuitry may apply to the automated suturing device 1740 as well.

The thread management system 1750 includes a tensioning device 1730 and a thread movement device 1720 that are together configured to clear a needle path of a thread and to apply one or more targeted tensions to the thread during a suturing procedure. The controller 1760 can provide the thread management system 1750 control signals to coordinate operation of the tensioning device 1730 and the thread movement device 1720 with the automated suture fixture 1705 and the automated suturing device 1740. The tensioning device 1730 and/or the thread movement device 1720 can include actuators to manipulate components of each device. In some embodiments, the actuators include motorized actuators which may operate in a manner similar to the motorized actuators 1702 and/or motors 1704 of the automated suture fixture 1705, and the description of these components as well as the rotor, servo feedback, and motor control circuitry may apply to the thread management system 1750 as well.

A suturing procedure can be performed after a suture system has been programmed with a certain procedure, program, or script. One or more computer components, such as one or more processors and/or memory devices, can be utilized to store and execute a procedure-directing script or program, such that a procedure script or program may be played back for an operator on-demand.

The procedure can include loading a suturing process script or program, which can be pre-programmed. The desired script or program can be loaded in various ways, e.g., by providing input to the system or a computer of the system to load the desired script or program from storage or memory.

The procedure can involve triggering the positioning of an automated suture fixture (or automated fixture) 1705 and/or executing a suturing operation or other operation or step.

Once the suturing operation or other operation or step has been executed, if the relevant suturing operation or other operation or step represents a final operation or step of the suturing procedure or other procedure, the process can end. However, if additional steps of the suturing operation or procedure or other operation or procedure remain, the process can repeat the triggering, positioning, or executing steps where a subsequent step of the suturing process or procedure can be triggered, such that the process can involve completion of subsequent step(s).

Example Method of Forming a Suture

Figure 14:
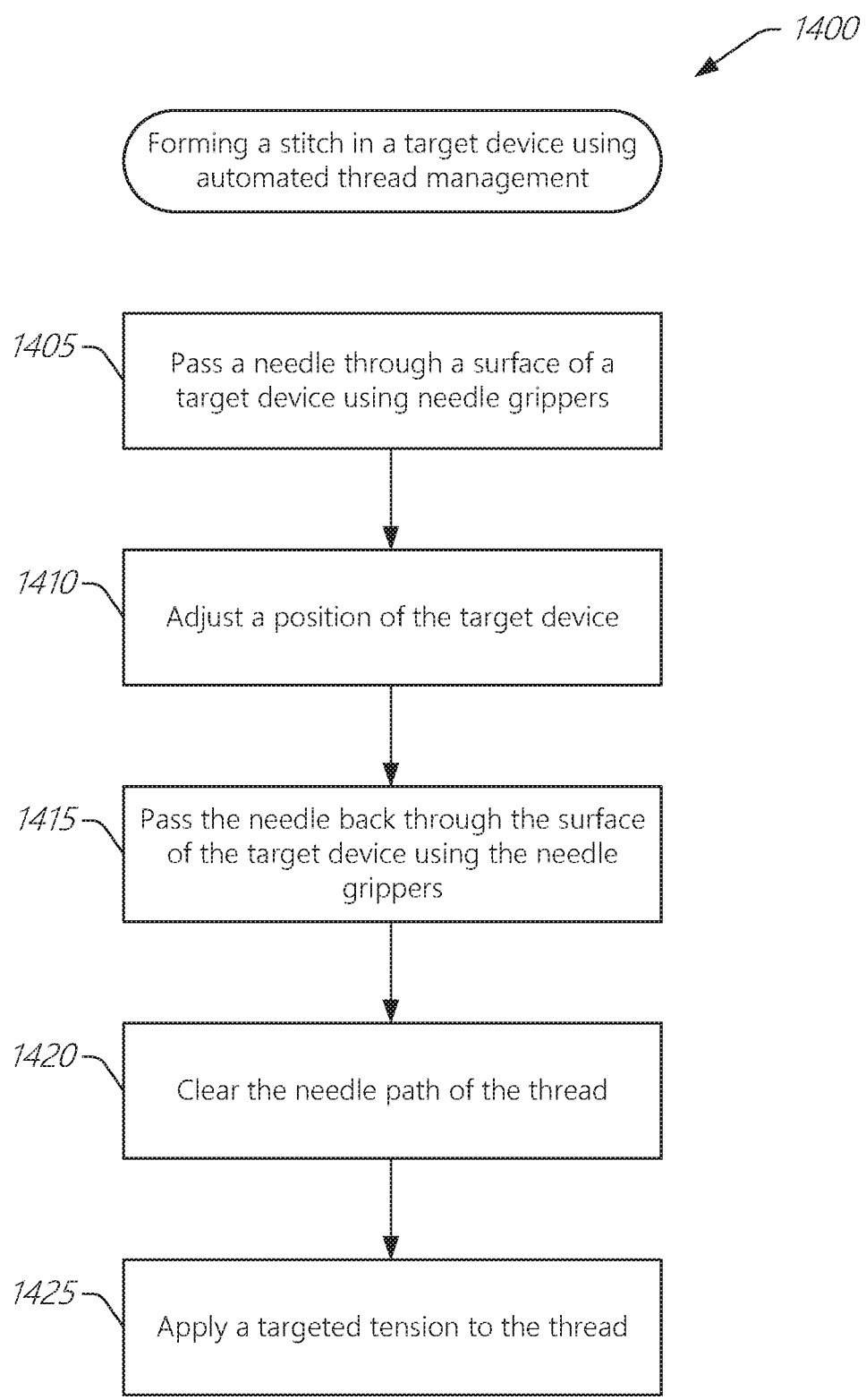
FIG. 14 illustrates a flow chart of an example method of forming a suture on an implant device using an automated thread management system.

FIG. 14 illustrates a flow chart of an example method 1400 of forming a suture on an implant device using an automated suturing system with a thread management system. Any of the automated suturing systems described herein can be used to perform the method 1400. For ease of description, the method 1400 will be described as being performed by an automated suturing system. However, it should be understood that any portion of an automated suturing system and/or any combination of components of an automated suturing system can perform any step, portion of a step, or combination of steps of the method 1400. Additional steps beyond those highlighted here are also possible, including steps described elsewhere herein, such as with respect to tension and thread management.

In block 1405, the automated suturing system passes a needle through a surface of a target device, the needle coupled to a thread that will form a stitch on the target device. The needle can be passed from a first needle gripper to a second needle gripper or any other suitable combination of needle gripping mechanisms. The path from the first needle gripper to the target device defines a needle path. In some embodiments, the needle path is a fixed linear path. The needle path can be a fixed linear path, a fixed curved path, or a fixed path with any combination of linear and curved portions.

In block 1410, the automated suturing system adjusts a position of the implant device to form the stitch. The position can be adjusted by rotating and/or moving the target device.

In block 1415, the automated suturing system passes the needle back through the surface of the target device. In some embodiments, the first needle gripper can return to a starting position along the same needle path.

In block 1420, the automated suturing system clears the needle path of the thread. In some embodiments, the needle path is cleared of the thread by moving a portion of the path between the target device and the needle perpendicular to the path of the needle.

In block 1425, the automated suturing system applies a targeted tension to the thread. In some embodiments, the targeted tension changes over the course of a suturing procedure. In some embodiments, the targeted tension is different during different portions of the method 1400. In some embodiments, the targeted tension includes providing tension that increases until reaching a threshold tension and then reducing the tension to a steady state or reduced tension. Applying targeted tension to the thread can include providing tension to the thread to maintain a stitch in a held down position while the outer needle gripper approaches the target device to avoid the needle from penetrating the previously-formed stitch. The step of block 1425 can be performed in various ways described and or shown herein. For example, the targeted tension can be applied as described herein with reference to FIGS. 11A and 11B. Thus, a first targeted tension can be applied during the steps of blocks 1405 and 1410 (e.g., a steady state tension), a second targeted tension can be applied during the step of block 1415 (e.g., the steady state tension or no tension), and a third targeted tension can be applied during the step of block 1420 (e.g., a tension that increases until reaching a threshold tension which then returns to the steady state tension).

Terminology and Additional Embodiments

As used herein, the terms sutures and stitches have been used interchangeably and include, for example and without limitation, a portion of thread through a fabric typically used to attach the fabric to a structure, to attach portions of fabric together, and/or to mend the fabric. As used herein, the terms suturing and sewing have been used interchangeably and include, for example and without limitation, the process of forming stitches or sutures on a target device. As used herein, the term target device has been used to refer generally to any implantable device or component thereof and includes, for example and without limitation, prosthetic implants, prosthetic human implant devices, prosthetic heart valves, prosthetic human heart valves, etc. As used herein, such as for target devices that are generally cylindrical or that otherwise form a lumen, reference to "inside the device" or to "an inner portion of the device" refers to positions enclosed and/or surrounded by a surface or structure of the device or that are within a lumen formed by a surface(s) or structure(s) of the device. Likewise, as used herein, reference to "outside the device" or to "an outer portion of the device" refers to positions that are not inside the device (e.g., external to or not enclosed by a surface or structure of the device or not within a lumen of formed by a surface or structure of the device).

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes. Moreover, in certain embodiments, acts or events can be performed concurrently rather than sequentially. For example, multi-threaded processing, interrupt processing, and/or multiple processors or processor cores could be used.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments do include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

The methods described herein include steps that are indicative of one or more embodiments of the presented method. Other steps and methods may be conceived that are equivalent in function, logic, or effect to one or more steps, or portions thereof, of the procedures or methods herein. Additionally, the order in which steps of a particular method occurs may or may not strictly adhere to the order of the corresponding steps described. Components, features, steps, etc. described with respect to one embodiment herein can be combined or included in other embodiments described elsewhere herein.

Components, aspects, features, etc. of the systems, assemblies, devices, apparatuses, methods, etc. described herein can be implemented in hardware, software, or a combination of both. Where components, aspects, features, etc. of the systems, assemblies, devices, apparatuses, methods, etc. described herein are implemented in software (e.g., scripts, etc.), the software can be stored in an executable format on one or more non-transitory machine-readable mediums. Further, the software and related steps of the methods described above can be implemented in software as a set of data and instructions. A machine-readable medium includes any mechanism that provides (e.g., stores and/or transports) information in a form readable by a machine (e.g., a computer). For example, a machine-readable medium includes read only memory (ROM); random access memory (RAM); magnetic disk storage media; optical storage media; flash memory devices; DVD's, electrical, optical, acoustical or other forms of propagated signals (e.g., carrier waves, infrared signals, digital signals, EPROMs, EEPROMs, FLASH, magnetic or optical cards, or any type of media suitable for storing electronic instructions. Information representing the units, systems, and/or methods stored on the machine-readable medium can be used in the process of creating the units, systems, and/or methods described herein. Hardware used to implement the invention can include integrated circuits, microprocessors, FPGAs, digital signal controllers, stream processors, and/or other components.

What is claimed is:

1. An automated suturing system comprising:
   a first automated fixture comprising a plurality of actuator devices and a holder, the first automated fixture being configured to adjust an orientation of a target device when mounted to the holder;
   a second automated fixture comprising a first needle gripper and a second needle gripper that are configured to pass a needle back and forth through a surface of the target device to form stitches with a thread coupled to the needle, the first needle gripper configured to trace a needle path; and
   a thread management system comprising a thread movement device having a support pin and configured to move the thread orthogonal to the needle path, the needle path being horizontal, and a tensioning device having a tensioning pin that is configured to push on the thread vertically to apply a tension to the thread to form a stitch in the target device, the thread configured to contact the support pin while the tensioning pin applies tension to the thread, the tensioning device configured to apply a first tension to the thread to secure the thread out of the needle path in conjunction with the thread movement device and to apply a second tension to pull the thread taut to form the stitch.

2. The automated suturing system of claim 1, wherein the target device is a heart valve or a component of a heart valve.

3. The automated suturing system of claim 1, wherein the tensioning pin is mounted to a tensioning bracket that moves relative to the thread movement device.

4. The automated suturing system of claim 1, wherein the automated suturing system is configured to repeatedly perform a suturing pattern to successively form sutures on the target device.

5. The automated suturing system of claim 4, wherein the tensioning device is configured to provide an increasing tension during a portion of the suturing pattern and to provide a steady state tension after the increasing tension exceeds a tension threshold.

6. The automated suturing system of claim 5, wherein the tension threshold is at least about 0.4 N.

7. The automated suturing system of claim 6, wherein the steady state tension is less than or equal to about 0.3 N.

8. The automated suturing system of claim 1, wherein the thread movement device includes two or more support pins that are configured to achieve a targeted direction for the tension relative to the thread, the targeted direction being substantially parallel to the needle path.

9. A thread management system comprising:
- a thread movement device comprising a support pin and configured to move a thread orthogonal to a needle path to clear the needle path for an automated suturing system, the needle path being horizontal; and
- a tensioning device comprising a tensioning pin that is configured to push on the thread vertically to apply a tension to the thread to form a stitch in a target device, the thread configured to contact the support pin while the tensioning pin applies tension to the thread, the tensioning device configured to apply a first tension to the thread to secure the thread out of the needle path in conjunction with the thread movement device and to apply a second tension to pull the thread taut to form the stitch.

10. The thread management system of claim 9, wherein the support pin is configured to achieve a targeted direction for the tension relative to the thread, the targeted direction being substantially parallel to the needle path.

11. The thread management system of claim 9, wherein the tensioning pin is mounted to a tensioning bracket that moves relative to the thread movement device.

12. The thread management system of claim 11, wherein the thread is configured to at least partially wrap around the tensioning pin to apply the tension to the thread.

13. The thread management system of claim 9, wherein the tensioning device is configured to provide an increasing tension until reaching a tension threshold and to provide a steady state tension after the increasing tension exceeds the tension threshold, the steady state tension being the first tension and the tension threshold being the second tension.

14. The thread management system of claim 9, wherein the thread movement device is configured to release the thread while the tensioning device applies the second tension to the thread.

15. An automated suturing system comprising:
- a first automated fixture and a holder, the first automated fixture being configured to adjust an orientation of a target device when held by the holder;
- a second automated fixture comprising a first needle gripper and a second needle gripper that are configured to pass a needle back and forth through a surface of the target device to form sutures with a thread coupled to the needle; and
- the thread management system of claim 9.

* * * * *